| (12) | United States Patent | (10) Patent No.: | US 12,084,488 B2 |
|---|---|---|---|
| | Lecommandoux et al. | (45) Date of Patent: | Sep. 10, 2024 |

(54) BIOCONJUGATES OF POLYSACCHARIDES AND ELASTIN-LIKE POLYPEPTIDES AND USES THEREOF

(71) Applicants: INSTITUT POLYTECHNIQUE DE BORDEAUX, Talence (FR); Centre national de la recherche scientifique, Paris (FR); UNIVERSITÉ DE BORDEAUX, Bordeaux (FR)

(72) Inventors: Sébastien Lecommandoux, Canejan (FR); Elisabeth Garanger, Talence (FR); Xiao Ye, Talence (FR)

(73) Assignees: INSTITUT POLYTECHNIQUE DE BORDEAUX, Talence (FR); Centre national de la recherche scientifique, Paris (FR); UNIVERSITÉ DE BORDEAUX, Bordeaux (FR)

( * ) Notice: Subject to any disclaimer, the term of this patent is extended or adjusted under 35 U.S.C. 154(b) by 629 days.

(21) Appl. No.: 17/279,653

(22) PCT Filed: Sep. 25, 2019

(86) PCT No.: PCT/EP2019/075865
§ 371 (c)(1),
(2) Date: Mar. 25, 2021

(87) PCT Pub. No.: WO2020/064836
PCT Pub. Date: Apr. 2, 2020

(65) Prior Publication Data
US 2021/0388056 A1 Dec. 16, 2021

(30) Foreign Application Priority Data
Sep. 25, 2018 (EP) .................................... 18306238

(51) Int. Cl.
*C07K 14/78* (2006.01)
*C08B 37/02* (2006.01)
*C08B 37/08* (2006.01)

(52) U.S. Cl.
CPC .......... *C07K 14/78* (2013.01); *C08B 37/0021* (2013.01); *C08B 37/0072* (2013.01)

(58) Field of Classification Search
CPC ................ C07K 14/78; A61K 47/6939; A61K 47/6935; A61K 38/00
See application file for complete search history.

(56) References Cited

FOREIGN PATENT DOCUMENTS

| CN | 106279439 A | 1/2017 | |
|---|---|---|---|
| EP | 1422242 A1 * | 5/2004 | .......... A61L 27/227 |
| JP | 2004-231633 A | 8/2004 | |
| JP | 2012-506940 A | 3/2012 | |
| WO | 2006/001806 A2 | 1/2006 | |
| WO | 2007/146228 A2 | 12/2007 | |

OTHER PUBLICATIONS

Malho et al., ACS Macro Lett., 2018, 7, 646-650 (Year: 2018).*
Extended European Search Report issued in corresponding European Patent Application No. 18 30 6238 dated Apr. 5, 2019.
International Search Report issued in corresponding International Patent Application No. PCT/EP2019/075865 dated Dec. 5, 2019.
Malho, J., et al. Multifunctional Stimuli-Responsive Cellulose Nanocrystals via Dual Surface Modification with Genetically Engineered Elastin-Like Polypeptides and Poly(acrylic acid) ACS Macro Lett 7:646-650 (2018) cited in EESR & ISR.
Wang, H. et al. "Covalently Adaptable Elastin-Like Protein-Hylauronic Ackd (ELP-HA) Hybrid Hydrogels with Secondary Thermoresponseive Crosslinking for Injectable Stem Cell Delivery" Adv. Funct. Mater. 24(1605609): 1-11 (2017) cited in EESR & ISR.

* cited by examiner

*Primary Examiner* — Sudhakar Katakam
(74) *Attorney, Agent, or Firm* — TROUTMAN PEPPER HAMILTON SANDERS LLP

(57) ABSTRACT

The present invention concerns a block copolymer having at least one oligo- or polysaccharide block and at least one elastin-like polypeptide block, wherein said block copolymer comprises at least one repetitive unit having the following formula (I):

(I)

wherein R' is the side chain of a natural or synthetic amino acid other than proline and derivatives thereof.

11 Claims, 14 Drawing Sheets

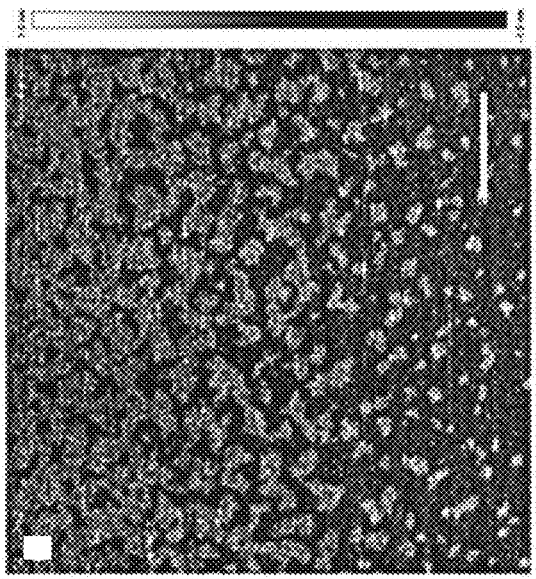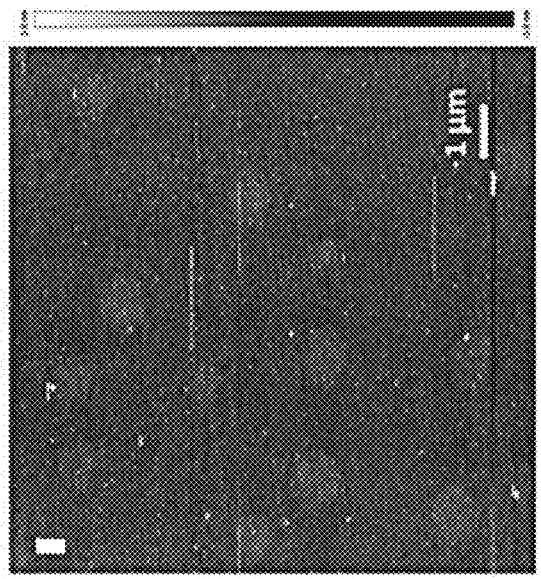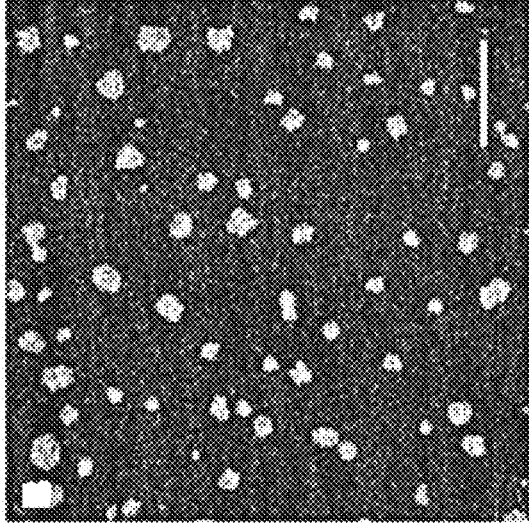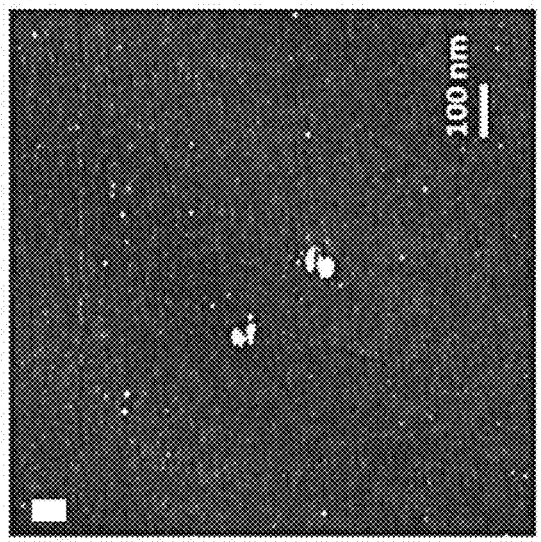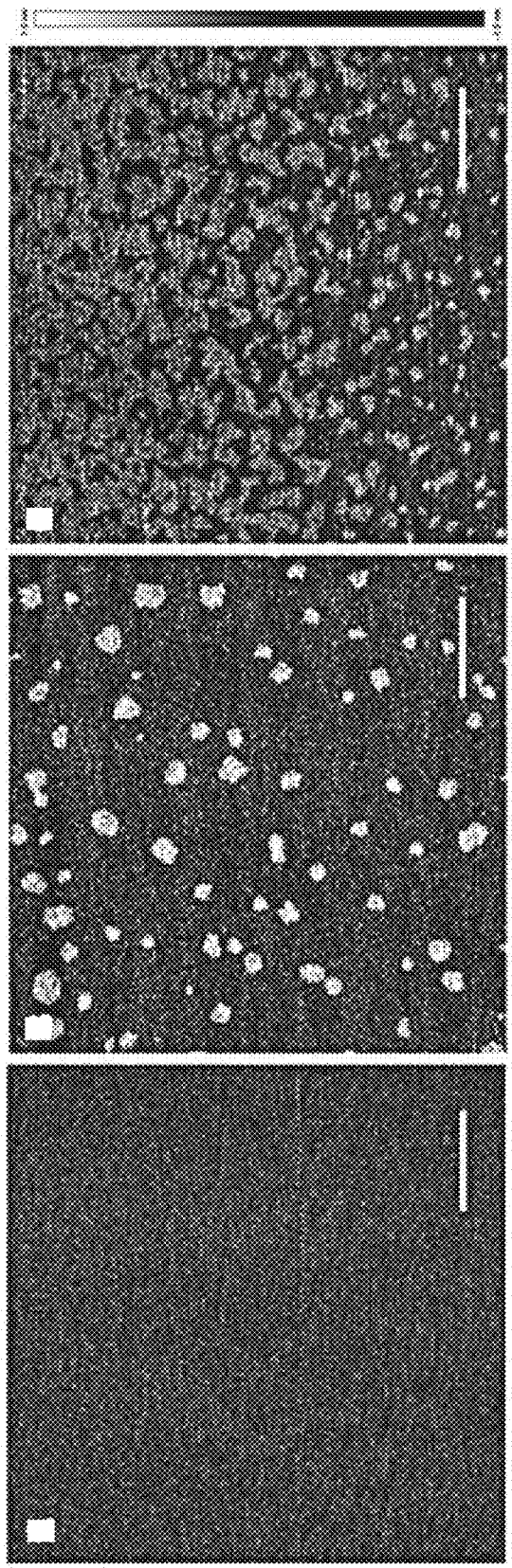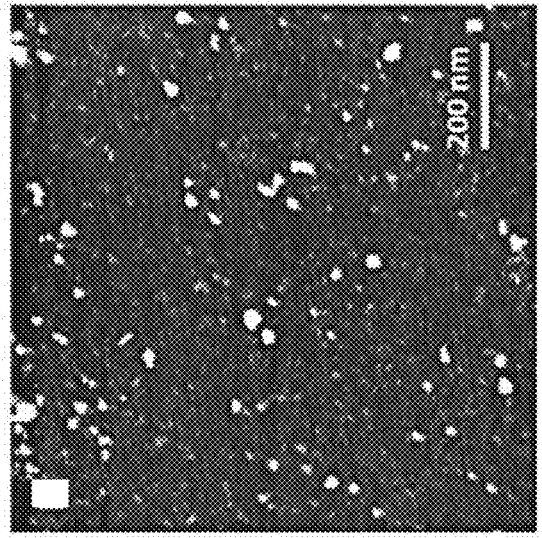

BIOCONJUGATES OF POLYSACCHARIDES AND ELASTIN-LIKE POLYPEPTIDES AND USES THEREOF

CROSS REFERENCE TO RELATED APPLICATIONS

The present application is a U.S. National Phase Application under 35 U.S.C. § 371 of International Patent Application No. PCT/EP2019/075865, filed Sep. 25, 2019, which claims priority of European Patent Application No. 18306238.9, filed Sep. 25, 2018. The entire contents of which are hereby incorporated by reference.

FIELD OF THE INVENTION

The present invention concerns bioconjugates of polysaccharides and elastin-like polypeptides, their preparation processes and uses thereof.

BACKGROUND

Recent advances in glycochemistry have led to the preparation of linear block copolymers, where polysaccharide chains are combined with a second, either synthetic or natural, block. A high degree of functionality can be obtained when the carbohydrate chains are copolymerized via click-chemistry with a predefined peptidic sequence, obtained for instance by recombinant DNA technology, which allows to obtain polypeptides with an exact primary structure.

This approach allows designing block copolymers with well-defined functionalities, and possibly intrinsic bioactivity, as well as stimuli responsiveness, which can be integrated in either or both blocks. By design, the solubility in water of the blocks can strongly differ and/or respond to changes in the physicochemical environment, leading to the formation of compartmentalized aggregates such as core-corona spherical or cylindrical aggregates, or vesicles.

In particular, elastin-like polypeptides (ELPs) have recently attracted much attention as temperature-responsive peptidic sequence, as they undergo a phase transition from a hydrated coil to a collapsed coacervate at a specific temperature (transition temperature, Tt). The lower critical solution temperature (LCST), corresponding to the minimum temperature in the phase diagram, can be controlled by the length and the primary sequence of the polypeptide, so that the transition temperature at a specific concentration can be adjusted as required.

In addition, due to their natural biocompatibility and biodegradability, polysaccharides and polypeptides based block copolymers are widely applied in the biomedical and biomaterials fields, for tissue engineering or drug delivery. Some polysaccharides recognize specific receptors (e.g. galactan/galectine or, hyaluronan/CD44), denoting great interest for the design of targeting copolymers.

SUMMARY

The aim of the present invention is to provide new block copolymers with temperature-induced self-assembly properties.

Another aim of the present invention is to provide block copolymers with a tunable LCST, and able to form nanoparticles depending on the temperature.

Another aim of the present invention is to provide materials with precise bioactivities and stimuli-responsive self-assembled properties in aqueous condition above a specific and tunable LCST.

BRIEF DESCRIPTION OF THE DRAWINGS

FIG. 1 scattering intensity as a function of temperature upon fast heating. FIG. 2 size distribution in intensity at various temperatures (30° C., 40° C., 45° C., 55° C., and 60° C.).

FIG. 10) Scattering intensity as a function of temperature upon fast heating. FIG. 11 Size distribution in intensity at various temperatures (25° C., 35° C., 48° C., and 60° C.).

FIGS. 14A-14F represent liquid AFM images of HA-ELP (150 µM in water) on mica substrate at (14A, 14D) 25° C., (14B, 14E) 52° C. or (14C, 14F) 55° C. The scale bar indicates 1 µm.

DETAILED DESCRIPTION

Figure 1:
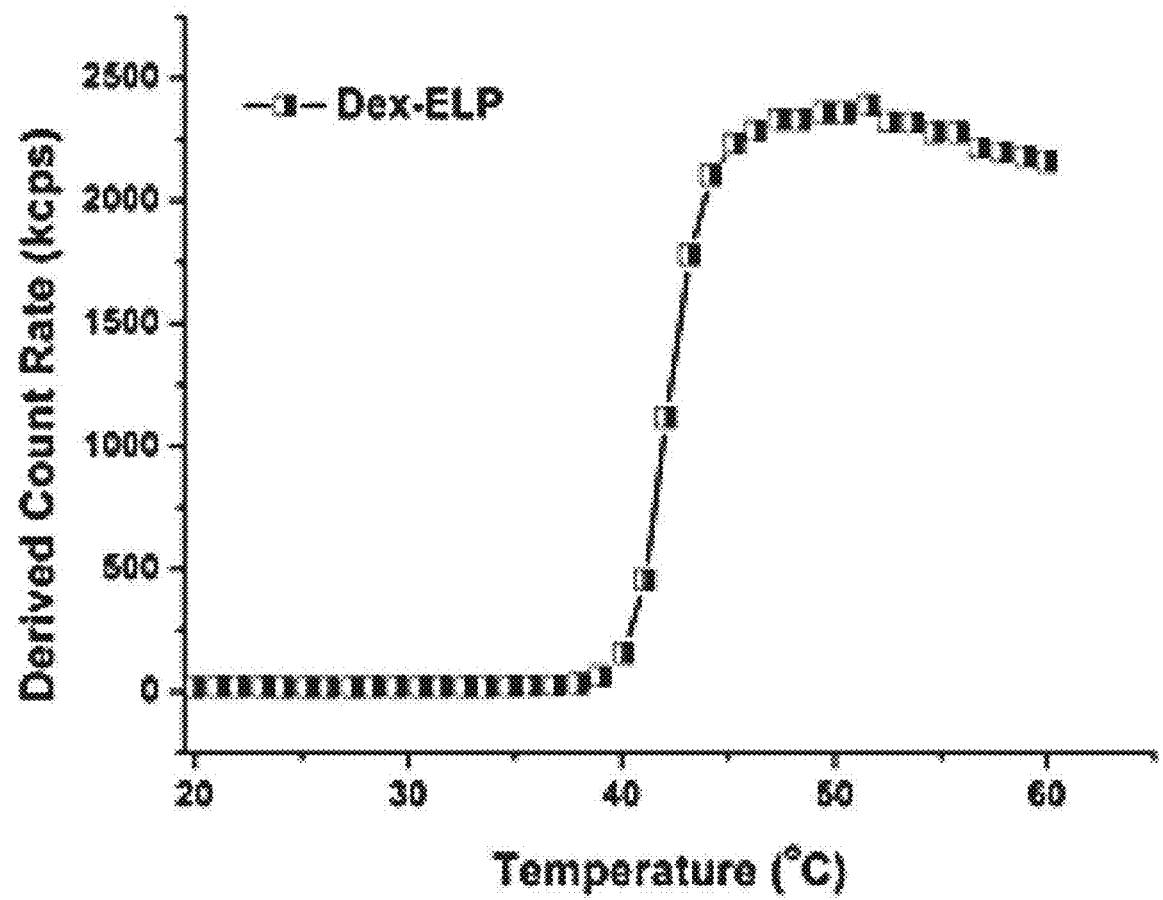
FIG. 1 and FIG. 2 represent the dynamic light scattering analysis of the assembly of Dex-ELP (125 µm) in water.

Therefore, the present invention relates to a block copolymer having at least one oligo- or polysaccharide block and at least one elastin-like polypeptide block, wherein said block copolymer comprises at least one repetitive unit having the following formula (I):

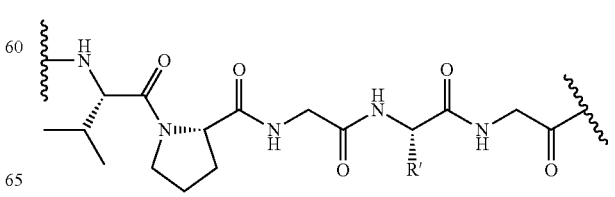

wherein R' is the side chain of a natural or synthetic amino acid other than proline and derivatives thereof.

The block copolymers according to the invention are thus conjugates comprising a polysaccharide (or oligosaccharide) block as well as a derivative of elastin-like polypeptide (ELP) corresponding to the repetitive unit of formula (I).

ELPs are repeating sequences of [-Val-Pro-Gly-Xaa-Gly-] pentapeptide, the guest residue Xaa being any amino acid except proline, originally inspired from the hydrophobic domain of tropoelastin (in the repetitive unit of formula (I) according to the invention, R' corresponds to the side chain of said Xaa amino acid).

ELPs exhibit a lower critical solution temperature (LCST), also referred as an inverse temperature transition (Tt), similar to synthetic polymers such as poly(N-isopropylacrylamide) (pNIPAM). ELP chains are fully soluble in water below the LCST, while switching to an insoluble state above the LCST. Fully reversible, the aggregation is influenced by different parameters such as the nature of the Xaa guest residues within the ELP repeats, the overall molecular weight and molar concentration of the ELP, and the ionic strength of the solution (Meyer, D. E.; Chilkoti, A. *Biomacromolecules* 2004, 5, 846-851; McDaniel, J. R.; Radford, D. C.; Chilkoti, A. *Biomacromolecules* 2013, 14(8), 2866-2872). This solubility switch has proven to be a major advantage for the purification of recombinant ELPs from bacterial lysates, as well as for the controlled self-assembly of individual ELP blocks.

According to the present invention, the expression "proline and derivatives" refers to proline as well as any cyclic α-amino acid.

The term "proline derivative" design any non-canonical amino-acid based on a proline backbone, i.e. proline with substituent(s) on the α, β, γ or δ carbon atoms, such as 4-hydroxyproline or α-methylproline.

Preferably, the Xaa amino acid is valine or methionine.

According to an advantageous embodiment, the block copolymer of the invention comprises at least one repetitive unit having the formula (I) wherein R' is —CH(CH$_3$)$_2$ or —(CH$_2$)$_2$SCH$_3$.

According to an embodiment, in the block copolymer of the invention, the oligo- or polysaccharide block and the elastin-like polypeptide block are linked together by a linker, said linker including a radical Y obtainable by click chemistry.

The radical Y is thus obtained by a click chemistry reaction. These click chemistry reactions include in particular the cycloadditions of unsaturated compounds, among which one may cite the Diels-Alder reactions between a dienophile and a diene, and especially also the azide-alkyne 1,3-dipolar cycloadditions, and preferably the copper-catalyzed azide-alkyne cycloaddition (CuAAC).

Other click chemistry reactions include reactions involving a thiol function such as the formation of thioethers from an alkene and mixed disulfides, and also reactions involving an electrophilic carbonyl group of the non-aldol type, for example the formation of oxime ethers from an oxyamine, of hydrazones from a hydrazine or also the formation of thiosemicarbazones from a thiosemicarbazine.

As click chemistry reactions, one may also cite reactions involving thiocarboxylic acids or thioesters to lead to the formation of thioesters and amides, and also the reactions between azides and phosphines (such as Staudinger ligations).

Preferably, the radical Y is obtained by the reaction between two reactive functions, said reaction being selected from the group consisting of:
the reaction between an azide and an alkyne,
the reaction between an aldehyde or ketone and a hydrazide,
the reaction between an aldehyde or ketone and an oxyamine,
the reaction between an azide and a phosphine,
the reaction between an alkene and a tetrazine,
the reaction between an isonitrile and a tetrazine, and
the reaction between a thiol and an alkene (thiol-ene reaction).

According to an embodiment, the block copolymer of the invention has the following formula (II):

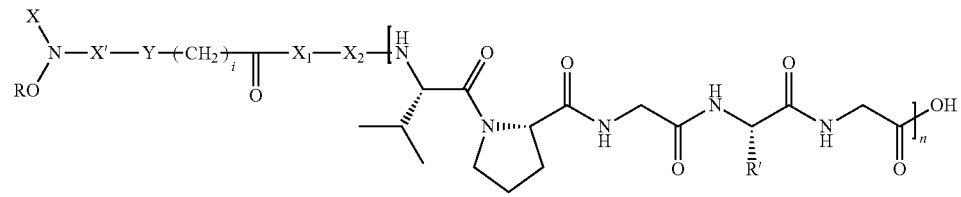

wherein:
R is a (C$_1$-C$_6$)alkyl group;
X is an oligo- or polysaccharide,
X' is a (C$_1$-C$_6$)alkylene radical,
Y is a radical selected from the group consisting of the following radicals:

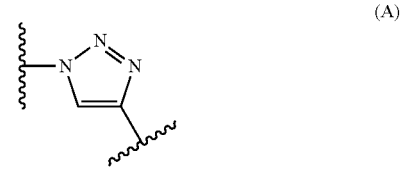

(A)

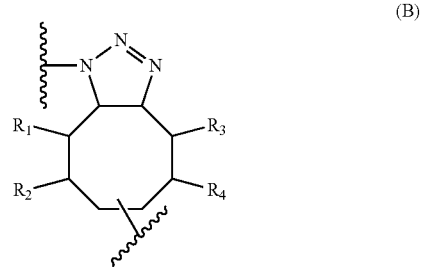

(B)

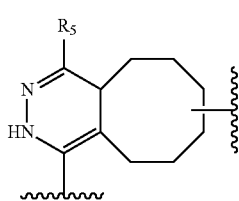
(C)

$R_1$ and $R_2$ being H or forming together with the carbon atoms carrying them a cyclohexyl radical;
$R_3$ and $R_4$ being H or forming together with the carbon atoms carrying them a cyclohexyl radical; and
$R_5$ being H or an alkyl group;
i is an integer between 1 and 6,
$X_1$ is a covalent bond or a radical of formula

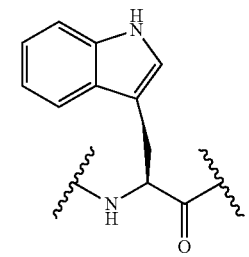

$X_2$ is a covalent bond or a radical of formula $-(AA)_j-$, j being an integer comprised between 1 and 6, and AA being independently a natural or synthetic amino acid, $X_2$ being preferably a radical of formula n is an integer between 1 and 200,
R' is as defined above in formula (I), and is preferably independently $-CH(CH_3)_2$ or $-(CH_2)_2SCH_3$.

According to the present invention, the expression "($C_t$-$C_z$)alkyl" means an alkyl group which can have from t to z carbon atoms.

Within the present application, the term "an alkyl group" means a linear or branched, saturated or unsaturated, hydrocarbon-based aliphatic group comprising, unless otherwise mentioned, from 1 to 6, preferably from 1 to 4 carbon atoms. By way of examples, mention may be made of methyl, ethyl, n-propyl, isopropyl, butyl, isobutyl, tert-butyl or pentyl groups.

As used herein, the term "alkylene" (or "alkylidene") refers to a divalent radical comprising from 1 to 6, preferably from 1 to 4 carbon atoms. When said radical is linear, it may be represented by the formula $(CH_2)_i$ wherein i is an integer varying from 1 to 6. The following alkylene radicals may be cited as example: methylene, ethylene, propylene, butylene, pentylene, or hexylene.

According to an embodiment, the radical Y as defined above is obtained from:
the reaction between an azide and an alkyne, in particular by copper-catalyzed azide-alkyne Huisgen 1,3-dipolar cycloaddition (CuAAc); preferably, such radical has the formula (A) as mentioned above;
the reaction between an azide and a cyclooctyne, in particular by strain promoted copper-free azide-alkyne [3+2] cycloaddition (SPAAc); preferably, such radical has the formula (B) as mentioned above; or
the reaction between a tetrazine and a transcyclooctyne, in particular by inverse electron demand Diels-Alder cycloaddition (iEDDA); preferably, such radical has the formula (C) as mentioned above.

More preferably, Y is selected from the triazole radicals, and most preferably having the formula (A).

According to an embodiment, the block copolymer of the invention has the following formula (III):

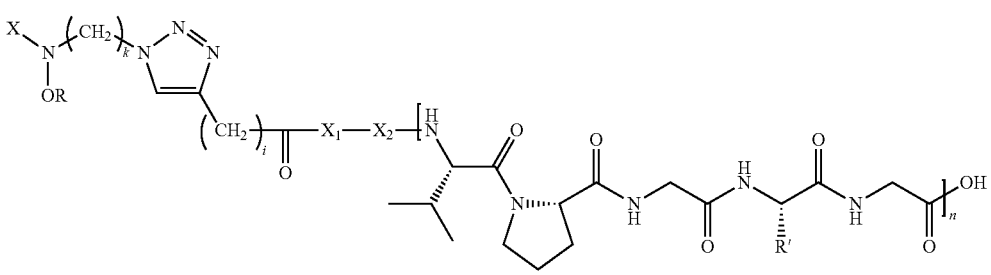

(III)

wherein:
k is an integer between 1 and 6, and
i, n, X, $X_1$, $X_2$, R, and R' are as defined above in formula (II).

According to an embodiment, the block copolymer of the invention has the following formula (III-1):

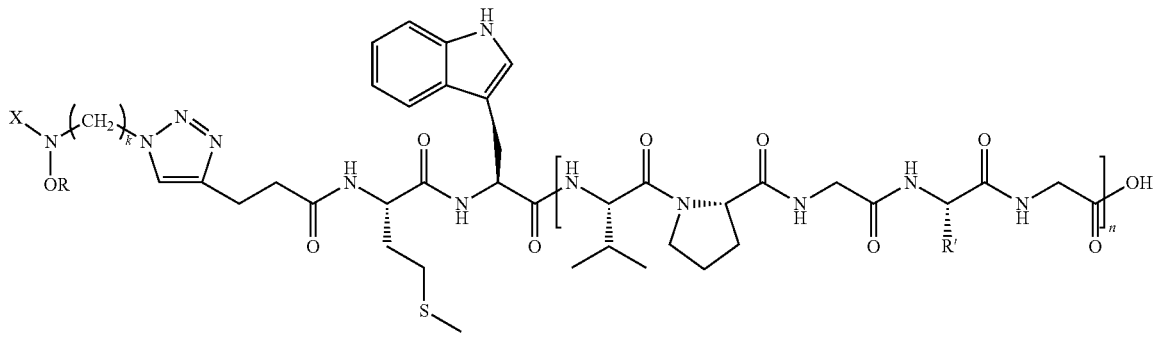

(III-1)

wherein:
k is an integer between 1 and 6, and
n, X, R, and R' are as defined above in formula (II).

Preferably, in the block copolymer according to the invention, in particular in formulae (II), (III) or (III-1), X is an oligosaccharide or polysaccharide selected from the group consisting of: galactans, glycoaminoglycans, cellulose, chitosan, fucoidan, and derivatives thereof.

More preferably, said oligosaccharide or polysaccharide is hyaluronan, laminarihexaose, dextran or a galactan, and most preferably is hyaluronan, laminarihexaose or a galactan.

According to an embodiment, the block copolymer according to the invention has one of the following formulae:

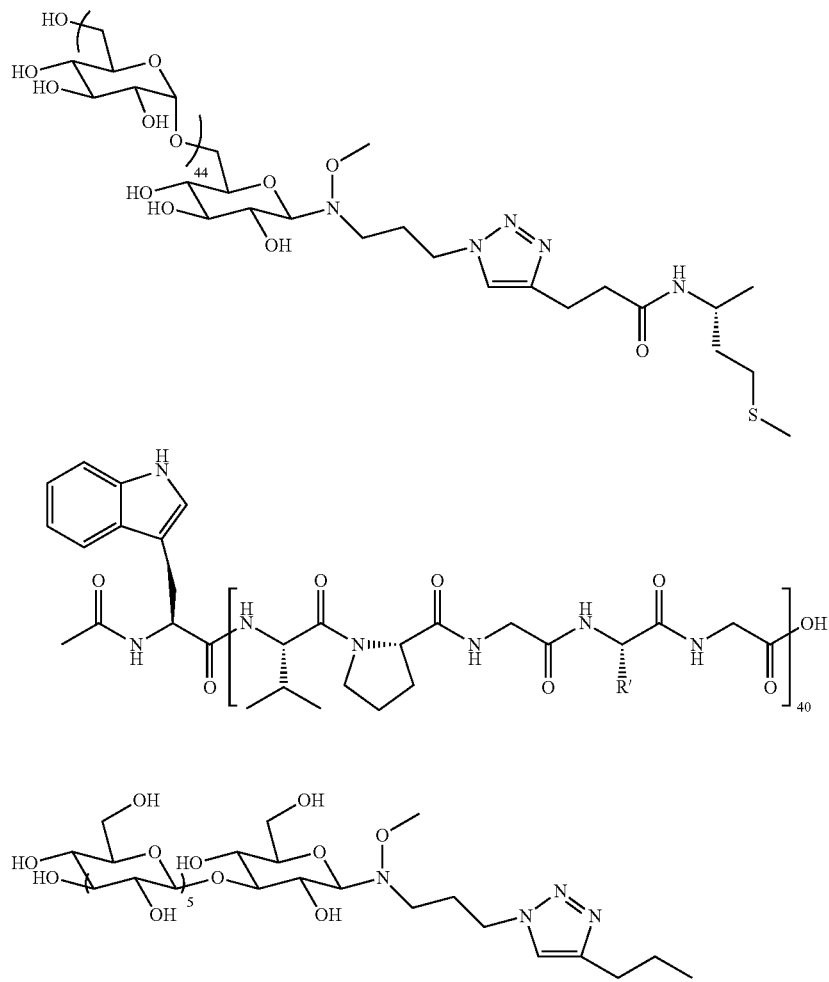

-continued

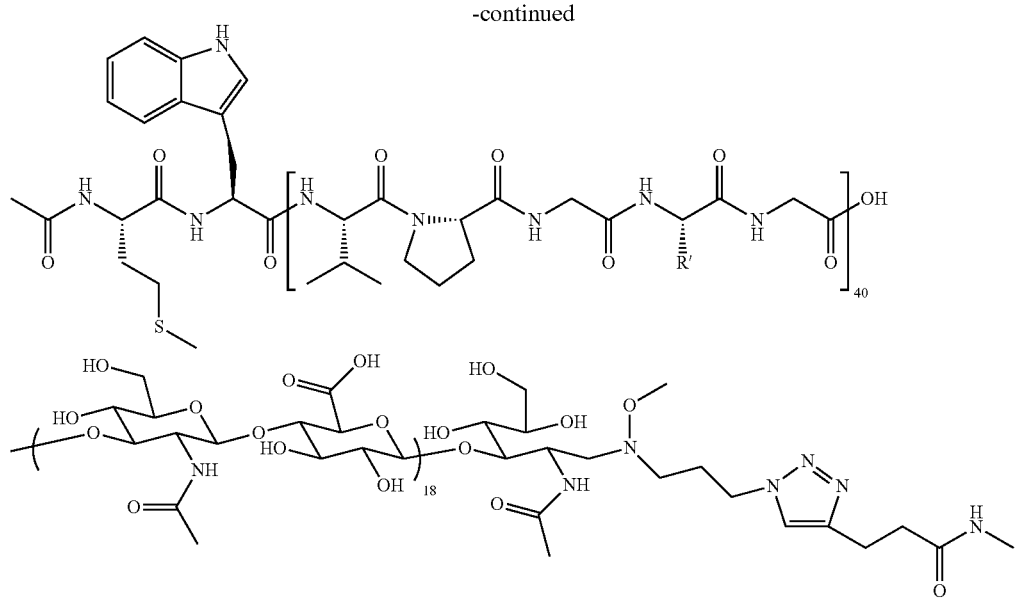

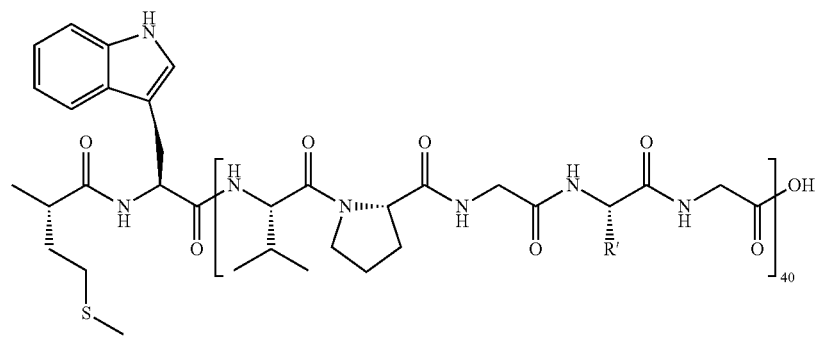

The present invention also relates to a method for the preparation of a block copolymer as defined above, comprising the reaction of a compound (1) carrying the oligo- or polysaccharide block and a functional group G1 with a compound (2) carrying at least one elastin-like polypeptide block and a functional group G2, wherein the functional groups G1 and G2 react together in order to form a linker by click chemistry.

More preferably, the present invention relates to a method for the preparation of a block copolymer as defined above, and having preferably the formula (II), comprising the reaction of a compound having the formula (IV):

wherein i, $X_1$, $X_2$, and R' are as defined above in formula (II), with an azide compound having the formula (V):

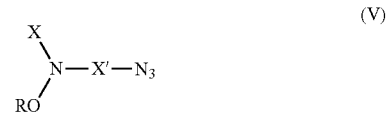

X, R, and X' being as defined in formula (II).

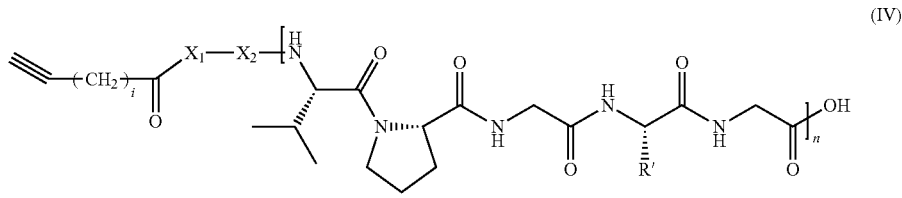

According to a preferred embodiment, the compound of formula (IV) is obtained by the reaction of a compound having the following formula (VI):

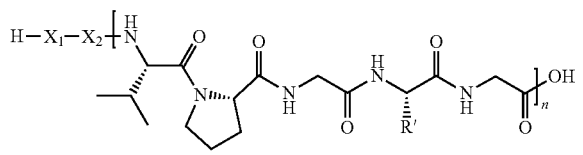

wherein $X_1$, $X_2$, and R' are as defined above in formula (II),
with a compound having the following formula (VII):

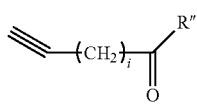

wherein:
i is as defined above in formula (II), and
R" is a leaving group.

In the above formula (VII), R" represents any leaving group, well-known in the art. Preferably, this radical is selected from the group consisting of the followings:
a radical derived from N-hydroxysuccinimide (NHS), such as the following radical:

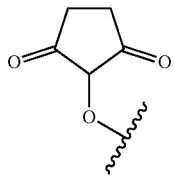

or a radical derived of pentafluorophenol, such as the following radical:

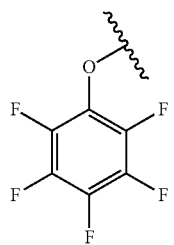 [SMILES: *Oc1c(F)c(F)c(F)c(F)c1F]

Other leaving groups also include chlorine atoms or radicals —OC(=O)—OAlk, Alk representing an alkyl group.

The present invention also relates to the use of a block copolymer as defined above, in particular having one of the formulae (II), (III) or (III-1), for the preparation of particles, such as nanoparticles or microparticles.

Preferably, said particles have an average diameter comprised between 10 nm and 10 μm, and more preferably between 50 nm and 500 nm, as measured by scattering (light, neutron) or microscopy techniques (AFM, Cryo-TEM).

The present invention also relates to a method for the preparation of (nano)particles of a block copolymer as defined above, comprising a step of heating the block copolymer above its transition temperature.

The particles, in particular micro- or nanoparticles, as obtained are particularly advantageous in that they may be used in various fields, such as for the stabilization of emulsions, but also for personal care or as nanocarrier in the healthcare. They may also be used in the cosmetic field.

According to an embodiment, these nanoparticles made of the block copolymer as defined above have an enhanced lectin-binding affinity as compared to the soluble form of said block copolymer.

Examples

The present invention is also described and demonstrated by way of the following examples. However, the use of these and other examples anywhere in the specification is illustrative only and in no way limits the scope and meaning of the invention or of any exemplified term.

Materials

Acrolein (95%), sodium azide ($NaN_3$, 99.5%), acetic acid (AcOH, 99.8%), methoxylamine hydrochloride (98%), sodium cyanoborohydride ($NaBH_3CN$, 95%), hydrochloric acid (HCl, 37%), 4-pentynoic acid (97%), N,N'-dicyclohexylcarbodiimide (DCC, 99%), N-hydroxysuccinimide (NHS, 98%), trimethylamine (TEA, 99%), copper(II) sulfate pentahydrate ($CuSO_4$, 99%), dichloromethane (DCM, 99.9%), N,N-dimethylformamide (DMF, 99.8%), dimethyl sulfoxide (DMSO, 99.7%), methanol (MeOH, 99.8%), diethyl ether (99.9%) and anhydrous magnesium sulfate ($MgSO_4$, 99.5%) were purchased from Sigma-Aldrich. N,N-Diisopropylethylamine (DIPEA, 99%), sodium acetate (AcONa, 99%) and sodium ascorbate (NaAsc, 99%) were obtained from Alfa Aesar. Methoxypolyethylene glycol (mPEG), tris(benzyltriazolylmethyl)amine (TBTA, 97%) and 4-toluenesulfonyl chloride (TsCl, 99%) were purchased from TCI. Cuprisorb® was purchased from Seachem. Dextran (Dex, T10) was purchased from pharmacosmos. Laminarihexaose (Hex) was purchased from Megazyme. Sodium hyaluronate (HA) was purchased from Lifecore Biomedical. Water was purified using an ELGA PURELAB Classic system. Solvent was purified using PureSolv MD-5 solvent purification system from Innovative Technology. Dialysis was conducted using a Spectra/Por®6 dialysis membrane.

Preparation of Compounds of Formula (V)
Preparation of an Azide Linker

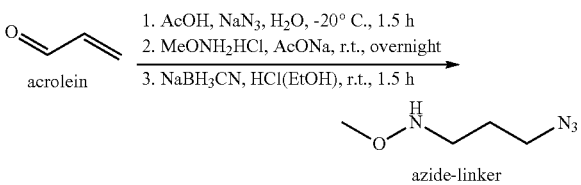

N-(3-azidopropyl)-O-methylhydroxylamine (azide-linker). Acetic acid (4 mL) in a round-bottom flask was cooled to −20° C. and acrolein (1.84 mL, 27.4 mmol) was added, followed by dropwise addition of a solution of sodium azide (2.38 g, 41.2 mmol) in $H_2O$ (10.4 mL). The mixture was continuously stirred at −20° C. for 1.5 h. Then it was quenched by addition of saturated sodium bicarbonate solution (sat. aq. $NaHCO_3$ 80 mL) and the resulting mixture was extracted with DCM (2×100 mL). The combined organic extracts were washed with sat. aq. NaHCO₃ (150 mL), dried over anhydrous MgSO₄, filtered and concentrated in vacuo to 100 mL. To the solution in DCM, methoxylamine hydrochloride (2.68 g, 31.68 mmol) and sodium acetate (4.42 g, 54 mmol) were added and the mixture was stirred at r.t for overnight. Sat. aq. NaHCO₃ (150 mL) was added to quench the reaction and the resulted mixture was then extracted with DCM (2×100 mL). The combined organic extracts were washed with Sat. aq. NaHCO₃ (150 mL), dried over anhydrous MgSO₄, filtered and concentrated in vacuo to 100 mL. To the solution in DCM, NaBH₃CN (2 g, 32 mmol) was added, followed by dropwise addition of 1M ethanolic HCl (32 mL, freshly prepared by adding acetyl chloride to ethanol). The resulting mixture was stirred at r.t for 1.5 h. Afterwards the solvent was removed by evaporator and the resulted white solid was suspended in sat. aq. NaHCO₃ (150 mL) and extracted with DCM (2×100 mL). The combined organic extracts were washed with sat. aq. NaHCO₃ (150 mL), dried over anhydrous MgSO₄, filtered and concentrated in vacuo to afford the crude N-(3-azidopropyl)-O-methylhydroxylamine as a yellow oil. Purification of the crude product by silica gel column chromatography (1-3% MeOH in DCM) yielded N-(3-azidopropyl)-O-methylhydroxylamine (azide-linker, 1.1 g, 62% over 3 steps) as a colorless oil.

$^1$H NMR (400 MHz, CDCl₃): δ 3.55 (s, 3H, CH₃O), 3.41 (t, 2H, CH₂N₃), 3.00 (t, 2H, NHCH₂), 1.83 (p, 2H, CH₂CH₂CH₂).

$^{13}$C NMR (101 MHz, CDCl₃): δ 62.01 (CH₃O), 49.44 (CH₂N₃), 48.94 (NHCH₂), 26.87 (CH₂CH₂CH₂).

Synthesis of Dextran-Azide

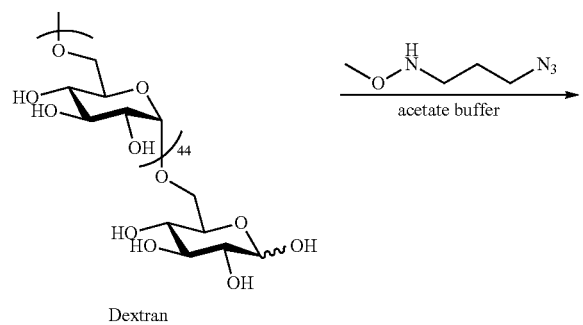

Dextran

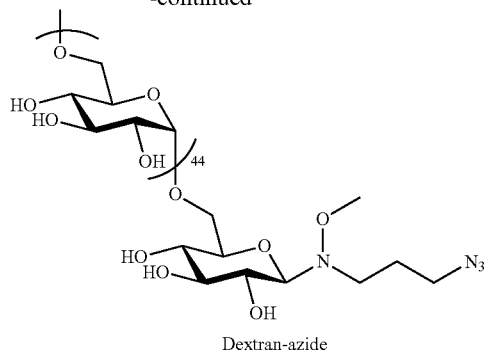

Dextran-azide

Dextran-azide (Dex-azide). To a solution of dextran (MW 8000) (1 g, 0.125 mmol) in acetate buffer (AcOH/AcONa, 2M, pH 4.6, 4.2 mL), azide-linker (380 mg, 2.9 mmol) was added and the reaction mixture was shaken on thermomixer at 40° C. for 9 days (vortexing 3 times per day). Then the mixture was purified by dialysis with a dialysis bag (MWCO 1000) against pure water for 24 h (changing water 3 times per day). The final product was obtained by lyophilization (white powder, 805 mg, 79% yield).

$^1$H NMR (400 MHz, D₂O): δ 4.98 (d, H-1), 4.18 (d, CHN(OCH₃)CH₂), 4.04-3.97 (m, H-6), 3.95-3.89 (m, H-5), 3.69-3.80 (br m, H-6', H-3), 3.61-3.37 (br m, H-2, H-4, CH₂N₃), 3.20-3.13 (dt, CHN(OCH₃)CH₂), 3.01-2.93 (dt, CHN(OCH₃)CH₂'), 1.92-1.88 (m, CH₂CH₂CH₂).

FT-IR (ATR): 3368, 2906, 2106 (u$_{azide}$), 1351, 1148, 1164, 1007, 915, 846, 763, 545, 429 cm$^{-1}$.

Synthesis of Laminarihexaose-Azide

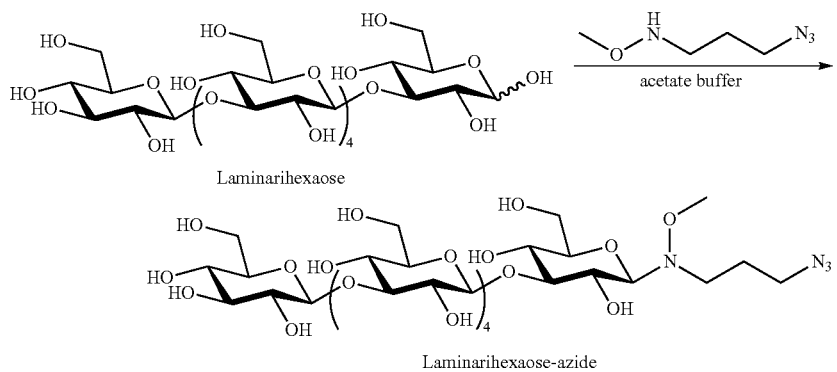

Laminarihexaose

Laminarihexaose-azide

Laminarihexaose-azide (Hex-azide). To a solution of laminarihexaose (500 mg, 0.5 mmol) in acetate buffer (AcOH/AcONa, 2M, pH 4.6, 5 mL), azide-linker (900 mg, 6.9 mmol) was added and the reaction mixture was shaken on thermomixer at 40° C. for 8 days (vortexing 3 times per day). Then the mixture was lyophilized and redissolved in water 5 mL, purified by dialysis with a dialysis bag (MWCO 100) against pure water for 36 h (changing water 3 times per day). The final product was obtained by lyophilization (white powder, 302 mg, 54% yield).

$^1$H NMR (400 MHz, D₂O): δ 4.81 (d, H-1), 4.23 (m, CHN(OCH₃)CH₂), 3.97-3.88 (m, H-6), 3.86-3.68 (br m, H-6', H-3), 3.67-3.33 (br m, H-2,H-4,H-5, CH₂N₃), 3.22-3.13 (m, CHN(OCH₃)CH₂'), 3.03-2.95 (m, CHN(OCH₃)CH₂), 1.91 (m, CH₂CH₂CH₂).

FT-IR (ATR): 3434, 3151, 2890, 2100 (u$_{azide}$), 1568, 1403, 1308, 1159, 1072, 1022, 896, 557 cm$^{-1}$.

Synthesis of Hyaluronan-Azide

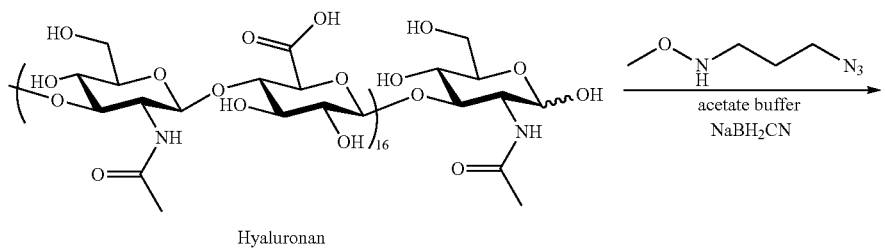

Hyaluronan

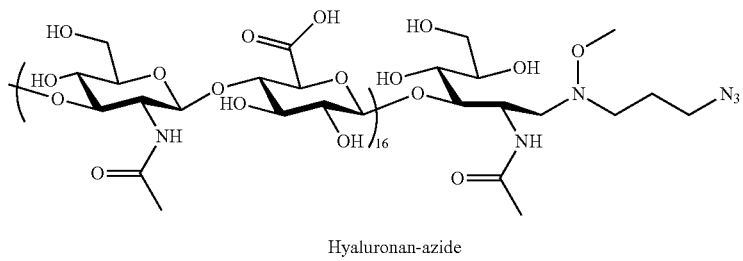

Hyaluronan-azide

Hyaluronan-azide (HA-azide). To a solution of sodium hyaluronate (MW 7000) (1 g, 0.14 mmol) in acetate buffer (AcOH/AcONa, 2M, pH 5.5, 5 mL), azide-linker (520 mg, 4 mmol) and sodium cyanoborohydride (65 mg, 1 mmol) were added and the reaction mixture was shaken on thermomixer at 50° C. for 5 days (vortexing 3 times per day). Then the mixture was diluted with water 5 mL, followed by dialyzing with a dialysis bag (MWCO 1000) against pure water for 24 h (changing water 3 times per day). The final product was obtained by lyophilization (white powder, 610 mg, 60% yield).

$^1$H NMR (400 MHz, D$_2$O): δ 4.56 (d, GlcNAc H-1), 4.48 (d, GlcUA H-1), 3.99-3.67 (br m, GlcNAc H-6, H-2, H-3, H-5, GlcUA H-4), 3.66-3.41 (br m, GlcNAc H-4, GlcUA H-3, H-5, CH$_2$N$_3$), 3.35 (t, GlcUA H-2), 2.94-2.86 (m, CH$_2$N(OCH$_3$)CH$_2$), 2.03 (s, GlcNAc COCH$_3$), 1.87 (m, CH$_2$CH$_2$CH$_2$).

FT-IR (ATR): 3323, 2892, 2107 (u$_{azide}$), 1729, 1642, 1555, 1376, 1315, 1152, 1042, 610 cm$^{-1}$.

Preparation of Compounds of Formula (IV)

1. Synthesis of Pentynoic NHS-Ester

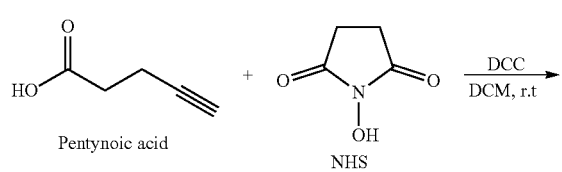

-continued

Pentynoic NHS-ester

Pentynoic NHS-ester. To a solution of pentynoic acid (210 mg, 2.14 mmol) in DCM (8 mL) was added N,N'-dicyclohexylcarbodiimide (480 mg, 2.3 mmol). The mixture was stirred for 5 mins and then N-hydroxysuccinimide (260 mg, 2.3 mmol) was added. The reaction was continuously stirred at r.t for 3 h. Afterwards, the precipitated dicyclohexylcarbamide was filtered off with Celite and the filter cake was washed with cold DCM (2×10 mL). The filtrate was collected and DCM was removed in vacuo. The product was redissolved in EtOAc (10 mL) and cooled in a refrigerator at 0° C. for 20 mins. The precipitate was filtered off again with Celite and the filtrate was washed with saturated NaHCO$_3$ (2×50 mL) and brine (2×50 mL), dried over anhydrous MgSO$_4$, filtered and concentrated in vacuo to give crude product as colorless oil. Purification of the residue by silica gel column chromatography (petroleum ether: EtOAc=2:1) yield pentynoic NHS-ester as a white solid (300 mg, 72% yield).

$^1$H NMR (400 MHz, CDCl$_3$): δ 2.90-2.82 (m, 6H, COCH$_2$CH$_2$CO, OCOCH$_2$CH$_2$), 2.62 (ddd, 2H, CH$_2$C≡CH), 2.05 (t, 1H, C≡CH).

$^{13}$C NMR (101 MHz, CDCl$_3$): δ 168.89 (COCH$_2$CH$_2$CO), 167.02 (OCOCH$_2$), 80.84 (CH$_2$C≡CH), 70.04 (CH$_2$C≡CH), 30.31 (OCOCH$_2$), 25.57 (COCH$_2$CH$_2$CO), 14.09 (CH$_2$C≡CH).

Synthesis of Alkyne-ELP

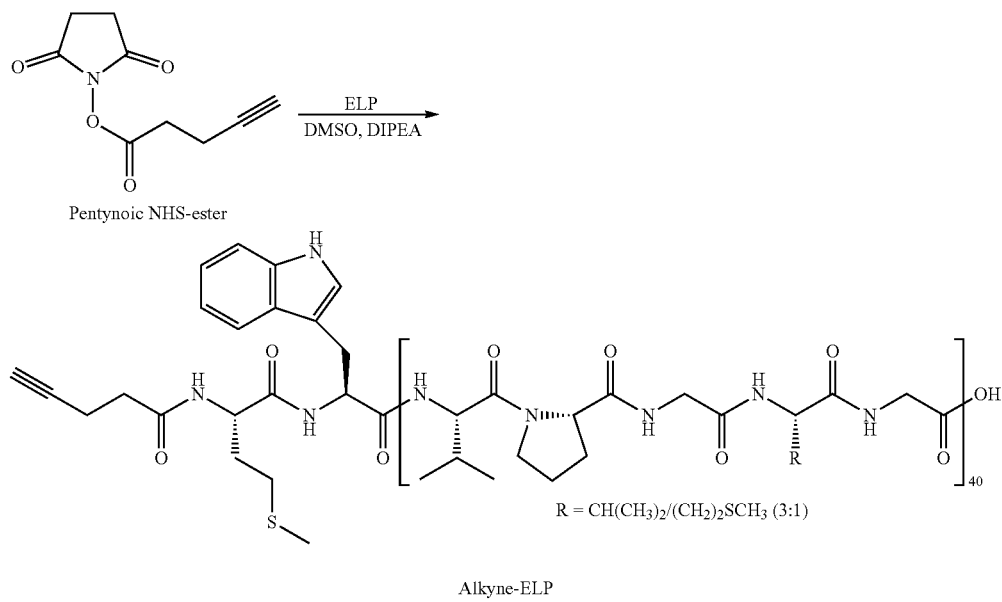

Alkyne-ELP (Alk-ELP). To a solution of ELP (225 mg, 13.2 μmol) in anhydrous DMSO (18 mL) was added pentynoic NHS-ester (92 mg, 0.47 mmol) and N,N-diisopropylethylamine (1.7 mg, 13.2 μmol). The reaction was stirred at r.t for 72 h. Then the mixture was diluted with water (20 mL) and the resulted solution was dialyzed against pure water in a dialysis bag (MWCO 15000) for 2 days (changing water 3 times per day). The final product was obtained by lyophilization (white powder, 210 mg, 93% yield).

$^1$H NMR (400 MHz, D$_2$O): δ 7.63-7.09 (br, indole H Trp), 4.57 (m, CHα Met), 4.45 (m, CHα Val, Pro), 4.19 (d, CHα Val Xaa), 4.06-3.89 (br m, CH$_2$α Gly, CH$_2$δ Pro), 3.75 (m, CH$_2$.δ Pro), 2.69-2.46 (br m, CH$_2$γ Met, CH$_2$CH$_2$C≡CH), 2.33 (m, CH$_2$β Pro), 2.18-1.91 (m, CH$_2$β Met, CH$_2$,β Pro CH$_2$γ Pro, CHβ Val, CH$_3$εMet, CH$_2$C≡CH), 1.05-0.91 (m, CH$_3$γ Val).

MALDI-TOF: Theoretical MW=17115 Da, Experimental [M+H]$^+$=17120.5 Da.

Preparation of Block Copolymers of Formula (II)

1. Synthesis of Dextran-b-ELP

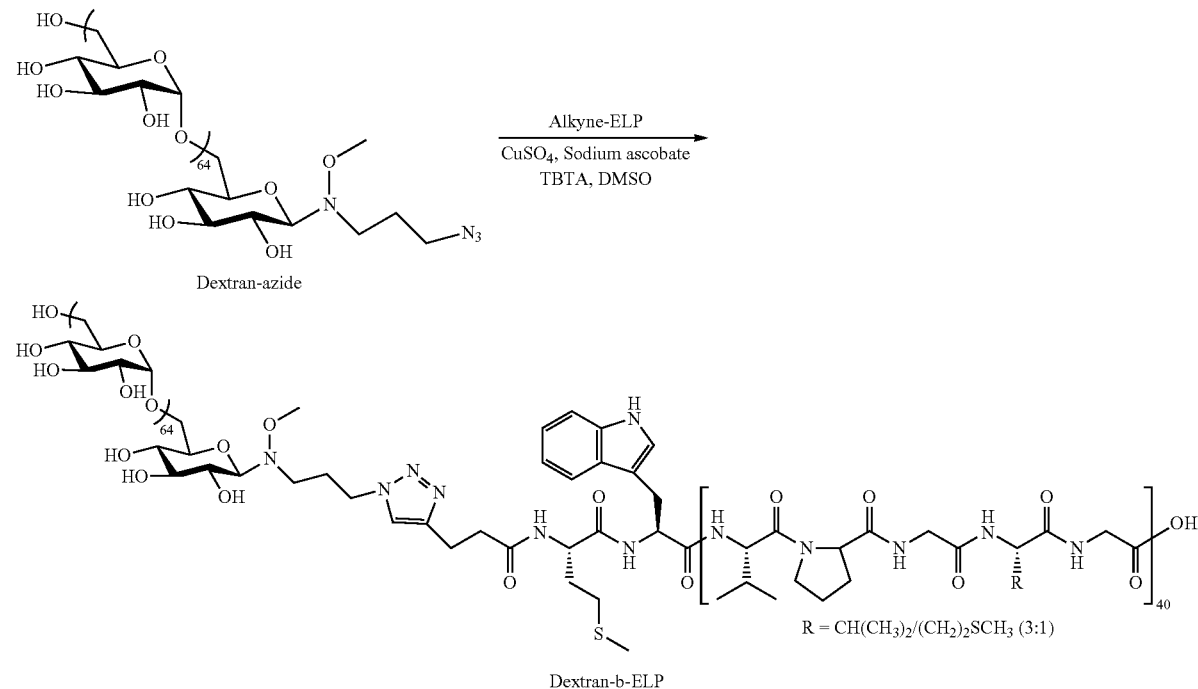

Dextran-b-ELP (Dex-ELP). Alkyne-ELP (65 mg, 3.8 µmol), dextran-azide (46 mg, 5.7 µmol), copper sulfate (6 mg, 22.8 µmol), sodium ascorbate (10 mg, 45.6 µmol) and TBTA (12 mg, 22.8 µmol) were dissolved in anhydrous DMSO (8 mL) under argon atmosphere. The mixture was stirred at r.t for 3 days. Then the mixture was diluted with cold water (20 mL) and cooled in a refrigerator at 4° C. for 20 mins. TBTA was precipitated and removed by centrifuge. Cuprisorb (120 mg) was added to the supernatant and the resulted solution was shaken at r.t for overnight to remove the copper. Cuprisorb was removed by centrifuge and the supernatant was dialyzed against pure water in a dialysis bag (MWCO 15000) for 5 days (changing water 3 times per day). The final product was obtained by lyophilization (white powder, 92 mg, 90% yield).

$^1$H NMR (400 MHz, D$_2$O): δ 7.75 (s, triazole H), 7.63-7.09 (br, indole H Trp), 4.99 (d, Dex H-1), 4.55 (m, CHα Met), 4.44 (m, CHα Val, Pro), 4.17 (d, CHα ValXaa), 4.06-3.87 (br m, CH$_2$α Gly, CH$_2$δ Pro, Dex H-6,H-5), 3.82-3.67 (m, CH$_2$δ Pro, Dex H-6',H-3), 3.62-3.49 (Dex H-2,H-4), 2.69-2.48 (br m, CH$_2$γ Met), 2.31 (m, CH$_2$β Pro), 2.18-1.89 (m, CH$_2$β Met, CH$_2$β Pro CH$_2$γ Pro, CHβ Val, CH$_3$ε Met), 1.03-0.88 (m, CH$_3$γ Val).

FT-IR (ATR): 3332, 2929, 1653, 1527, 1443, 1342, 1152, 1106, 1017, 917, 547 cm$^{-1}$.

Synthesis of Laminarihexaose-b-ELP

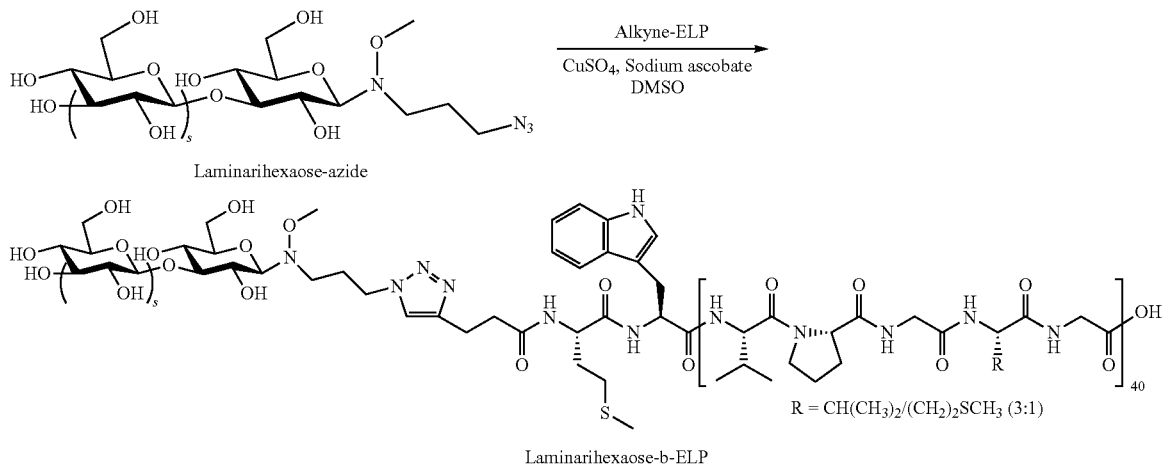

Laminarihexaose-b-ELP (Hex-ELP). Alkyne-ELP (62 mg, 3.6 µmol), laminarihexaose-azide (20 mg, 18.1 µmol), copper sulfate (5.5 mg, 22 µmol) and sodium ascorbate (9 mg, 45.4 µmol) were dissolved in anhydrous DMSO (8 mL) under argon atmosphere. The reaction was stirred at r.t for 3 days. Then the mixture was diluted with cold water (20 mL). Cuprisorb (110 mg) was added to the mixture and the resulted solution was shook at r.t for overnight to remove the copper. Cuprisorb was removed by centrifuge and the supernatant was dialyzed against pure water in a dialysis bag (MWCO 15000) for 5 days (changing water 3 times per day). The final product was obtained by lyophilization (white powder, 60 mg, 93% yield).

1H NMR (400 MHz, D$_2$O): δ 7.74 (s, triazole H), 7.60-7.09 (br, indole H Trp), 4.80 (m, Hex H-1), 4.55 (m, CHα Met), 4.43 (m, CHα Val, Pro), 4.17 (d, CHα ValXaa), 4.05-3.85 (br m, CH$_2$α Gly, CH$_2$δ Pro, Hex H-6), 3.82-3.66 (m, CH$_2$δ Pro, Hex H-6',H-3), 3.62-3.34 (Hex H-2,H-4, H-5), 2.69-2.48 (br m, CH$_2$γ Met), 2.41-2.24 (m, CH$_2$β Pro), 2.19-1.88 (m, CH$_2$β Met, CH$_2$β Pro CH$_2$γ Pro, CHβ Val, CH$_3$ε Met), 1.05-0.85 (m, CH$_3$γ Val).

FT-IR (ATR): 3322, 2917, 1654, 1522, 1440, 1221, 1105, 1063, 1027, 562 cm$^{-1}$.

Synthesis of Hyaluronan-b-ELP

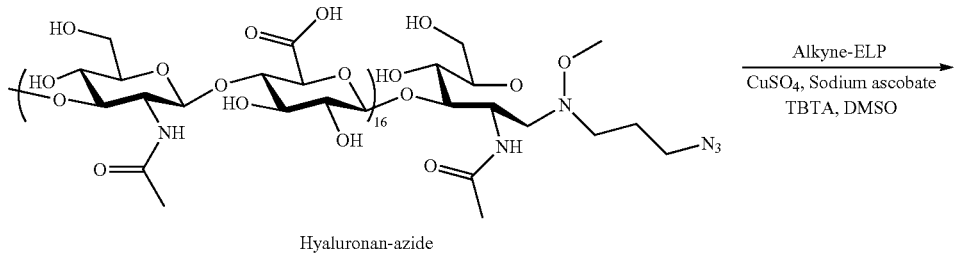

-continued

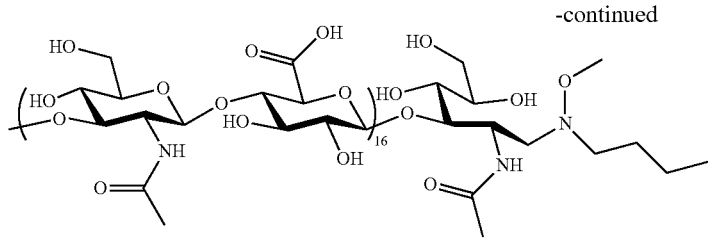

Hyaluronan-6-ELP

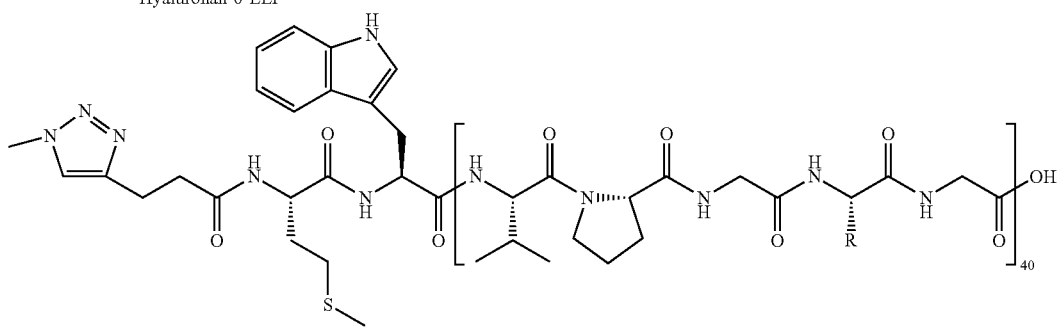

R = CH(CH₃)₂(CH₃)₂₈CH₃ [3:1]

Hyaluronan-b-ELP (HA-ELP). Hyaluronan-azide was first acidified by adding aq. HCl, so as to be totally soluble in DMSO. Alkyne-ELP (60 mg, 3.5 µmol), copper sulfate (9 mg, 36 µmol), sodium ascorbate (18 mg, 90 µmol) and tris(benzyltriazolylmethyl)amine (TBTA, 22 mg, 41 µmol) were dissolved in anhydrous DMSO (4 mL) under argon atmosphere. A solution of hyaluronan-azide (18 mg, 3.5 µmol) fully soluble in anhydrous DMSO (2 mL) was added. The reaction was stirred at 40° C. for 4 days. Then the mixture was diluted with cold water (20 mL) and cooled in a refrigerator at 4° C. for 20 mins. TBTA was precipitated and removed by centrifuge. Cuprisorb (180 mg) was added to the supernatant and the resulted solution was shaken at r.t for overnight to remove the copper. Cuprisorb was removed by centrifuge and the supernatant was dialyzed against pure water in a dialysis bag (MWCO 15000) for 5 days (changing water 3 times per day). The crude product was obtained by lyophilization (white powder, 53 mg). Deionized water (5.3 mL) was added and the solution was heated to 40° C. and kept for 1 h. The insoluble unreacted ELPs were removed by centrifuge at 40° C. and the supernatant was lyophilized to give the final product (white powder, 42 mg, 54% yield).

$^1$H NMR (400 MHz, D$_2$O): δ7.75 (s, triazole H), 7.60-7.09 (br, indole H Trp), 4.62-4.37 (br, CHα Met, Val, Pro, GlcUA H-1, GlcNAc H-1), 4.17 (d, CHα ValXaa), 4.04-3.66 (br, CH$_2$a Gly, CH$_2$δ Pro, CH$_2$.δ Pro, GlcUA H-4, GlcNAc H-2, H-3, H-5, H-6), 3.65-3.42 (GlcUA H-3, H-5), 3.41-3.30 (t, GlcUA H-2), 2.69-2.48 (br m, CH$_2$γ Met), 2.41-2.25 (m, CH$_2$β Pro), 2.20-1.89 (m, CH$_2$β Met, CH2'β Pro CH$_2$γ Pro, CHβ Val, CH$_3$ε Met), 1.06*0.88 (m, CH$_3$γ Val).

FT-IR (ATR): 3298, 2964, 1631, 1528, 1440, 1232, 1153, 1044, 541 cm$^{-1}$.

Preparation of Particles
Temperature-Induced Self-Assembly Study.

The temperature-induced self-assembly of polysaccharide-ELP bioconjugates (corresponding to the block copolymers according to the invention) in water were studied via dynamic light scattering (DLS), static light scattering (SLS) and liquid atomic force microscopy (liquid AFM).

Experimental Methods
Dynamic Light Scattering Measurements (DLS)

Dynamic light scattering measurements were performed on NanoZS instrument (Malvern, U.K.) at a 90° angle at a constant position in the cuvette (constant scattering volume). The derived count rate (DCR) was defined as the mean scattered intensity normalized by the attenuation factor. The DCR was plotted against temperature and the T$_t$ is defined as the temperature corresponding to the point where the DCR starts increasing on this plot.

Static Light Scattering (SLS)

Static light scattering measurements were performed using an ALV/CG6-8F goniometer, with a full digital correlator in combination with a Spectra Physics laser (emitting vertically polarized light at λ=632.8 nm) and a thermostated bath controller (ranging from 20 to 50° C.). The data were acquired with the ALV correlator software, the counting time was typically 15 seconds at each different scattering angles ranging from 30° to 150°, in 10 increments. Hydrodynamic radius (Rh) was determined from the apparent diffusion coefficient and the Stokes-Einstein equation. The radius of gyration (Rg) was determined from a Guinier plot resulting from the measurement of the average scattered intensity at the same angles.

Temperature-Controlled Liquid Atomic Force Microscopy (Liquid AFM)

Temperature-controlled liquid atomic force microscopy measurements were performed using a Dimension FastScan Bruker AFM system. The topography images of the bioconjugates were obtained in Peak Force tapping mode, using a Silicon cantilever (ScanAsyst-Fluid+, Bruker) with a typical tip radius of 5 nm. The cantilever resonance was 150 kHz and the spring constant was 0.7 N/m. Substrates were purchased from Agar Scientific. Samples were prepared by drop-casting a bioconjugates water solution of 50 µM (150 µM for HA-ELP) onto a freshly cleaved mica or HOPG surface, which was directly applied for imaging. AFM imaging process was conducted in liquid environment at specific temperature. An external heating stage (Bruker) was used to achieve the target temperature at the substrate surface.

Experimental Results

Self-Assembly Study of Dex-ELP

Upon fast heating ramp on DLS, the transition temperature ($T_t$) of Dex-ELP (125 µM in water) was found around 40° C., which is higher when compared to the $T_t$ of ELP and physical mixture. Indeed, conjugation of a hydrophilic block to ELP resulted in an addition of the $T_t$.

Figure 2:
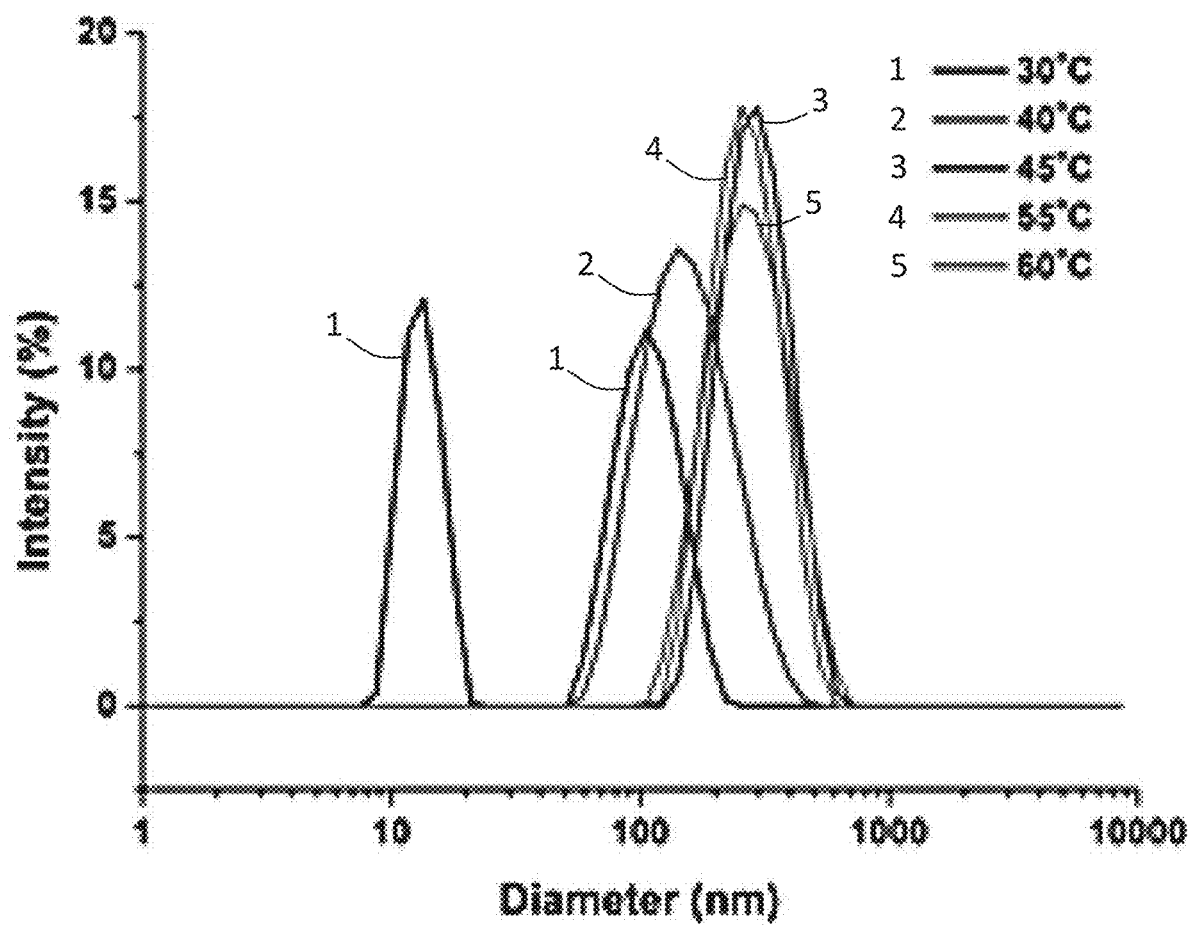

At low temperature below $T_t$ of Dex-ELP, small objects and a few aggregates were observed with very low scattering intensity (30° C.). The scattering intensity sharply increased at transition temperature (around 40° C.) and triggered the self-assembly to form structures with hydrodynamic diameter ($D_h$) around 165 nm. Once Dex-ELP was heated above 45° C., the nanoparticles showed little changes in diameter with a $D_h$ of approximately 290 nm (FIGS. 1-2).

Figure 3:
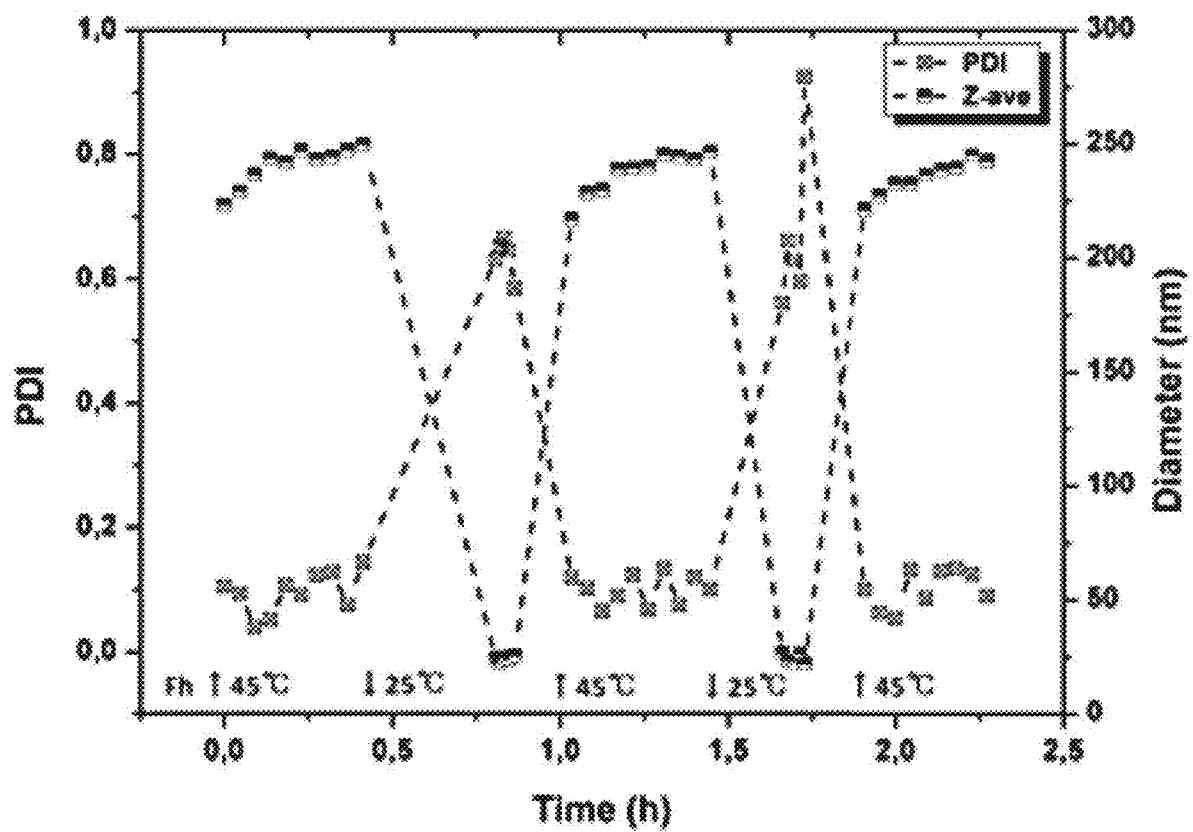
FIG. 3 represents Z-average size and polydispersity as a function of time upon repeated fast heating (45° C.) and cooling (25° C.) of Dex-ELP (125 µM) in water on DLS.
Figure 4:
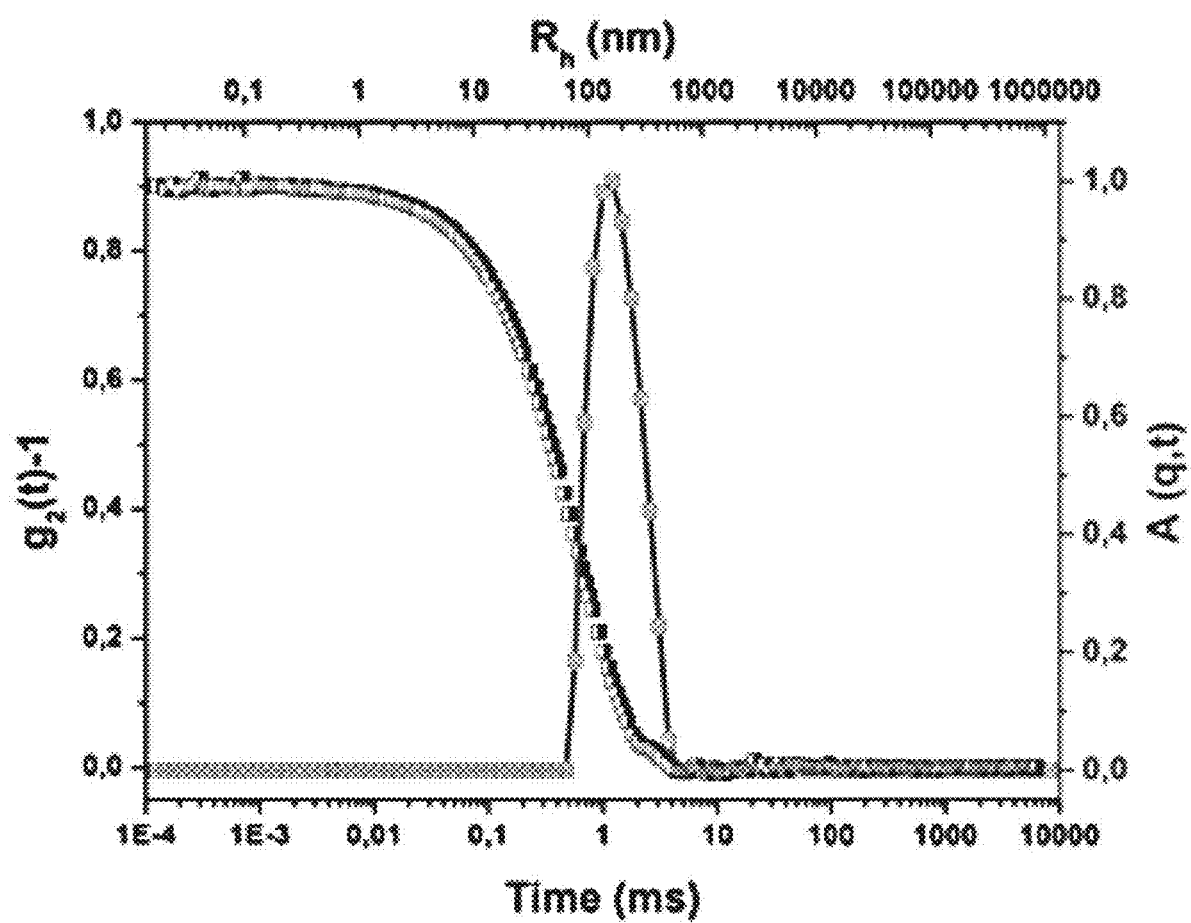
FIG. 4 represents DLS autocorrelation function $(g_2(t)-1)$ and relaxation-time distribution $(A(q,t))$ for Dex-ELP (125 µM) in water at 45° C., 90°.

The stability of the Dex-ELP assemblies above transition temperature was investigated by conducting various heating methods. The whole heating ways reached a $D_h$ around 300-330 nm in 30 mins and did not show significant difference on PDI. DLS cooling ramp showed slow disassemble behavior of Dex-ELP. Repeated heating and cooling DLS measurements were performed on the Dex-ELP solution to test the reversibility of the temperature-responsive system (FIGS. 3-4). At beginning, Dex-ELP was fast assembled to nanoparticles and stabled after 5 mins with an average diameter around 250 nm at 45° C. Afterwards, Dex-ELP nanoparticles were cooled to 25° C. and kept for 10-15 mins in order to fully disassemble the assemblies. Small objects with an average diameter below 25 nm and high PDI were observed at 25° C. Repeated heating and cooling again showing similar behavior illustrated that this temperature-responsive behavior is fully reversible which offering a simple method for controlling the temperature transition of ELPs.

Subsequently, the Dex-ELP assemblies were analyzed by SLS at 45° C. to determine the radium of gyration ($R_g$) and the hydrodynamic radius ($R_h$). $R_g/R_h$ ratio was calculated to be 0.72, indicating micelle structure.

Liquid atomic force microscopy was conducted to investigate the morphology of the nanostructures formed by the transition of ELP below/above $T_t$. Consistent with the DLS results, very small objects were showed below $T_t$ at 35° C., and spherical-shaped particles were observed with an average diameter of approximately 280-300 nm above $T_t$ at 65° C. (FIGS. 6A-6D).

Self-Assembly Study of Hex-ELP

Figure 5A:
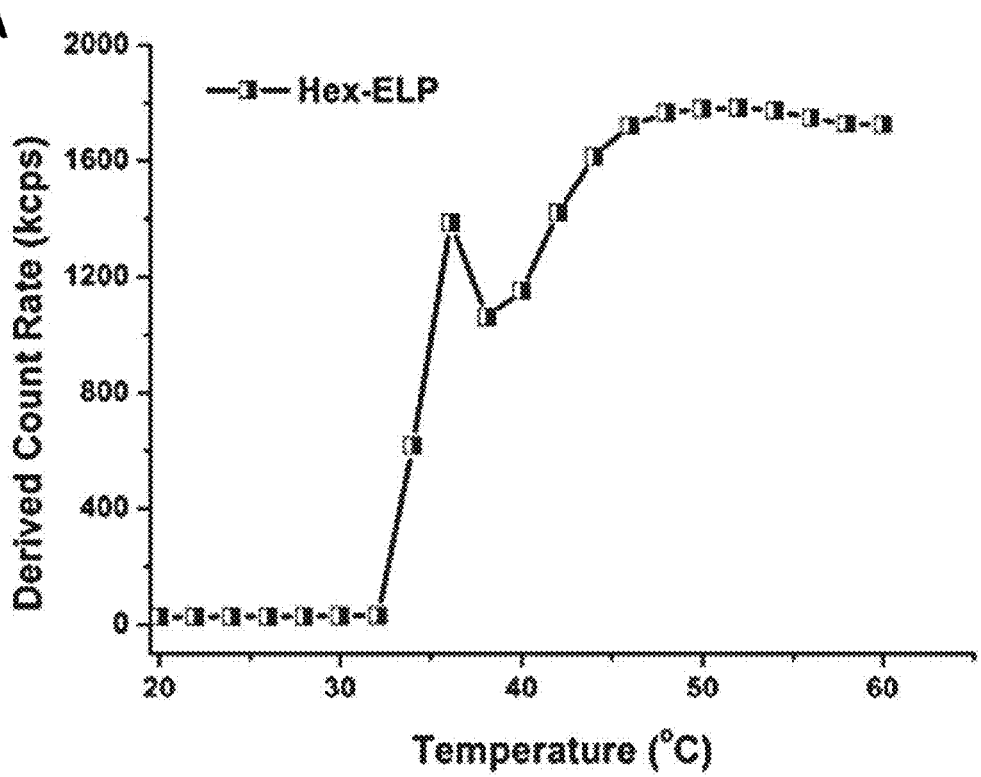
FIGS. 5A and 5B represent the dynamic light scattering analysis of the assembly of Hex-ELP (125 µM) in water. (5A) Scattering intensity as a function of temperature upon fast heating. (5B) Size distribution in intensity at various temperatures (30° C., 33° C., 37° C., 42° C., 50° C., and 60° C.).
Figure 5B:
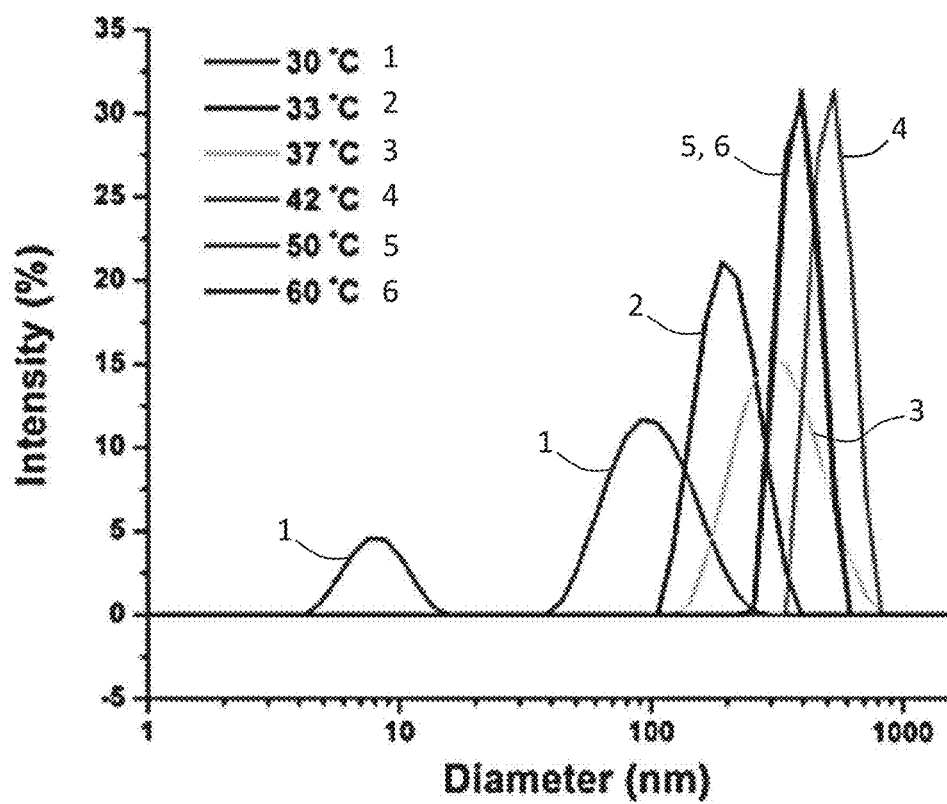
Figure 6A:
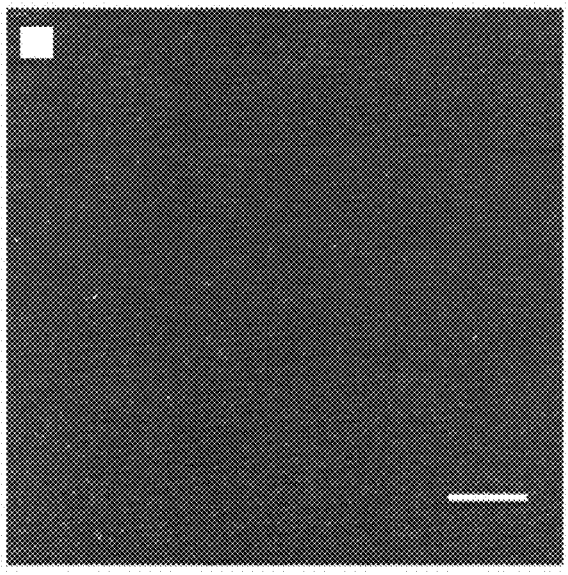
FIGS. 6A-6D represent liquid AFM images of Dex-ELP (50 µM in water) on mica substrate at (6A) 35° C. or (6B) 65° C., and of Hex-ELP (50 µM in water) on HOPG substrate at (6C) 30° C. or (6D) 55° C. The scale bar indicates 1 µm.
Figure 6B:
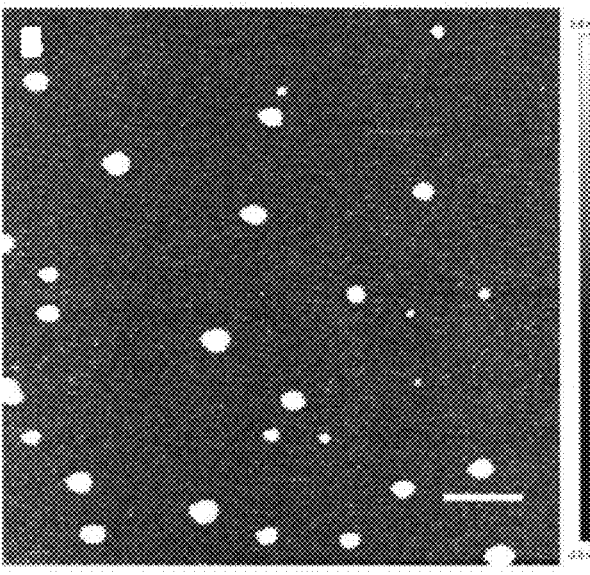
Figure 6C:
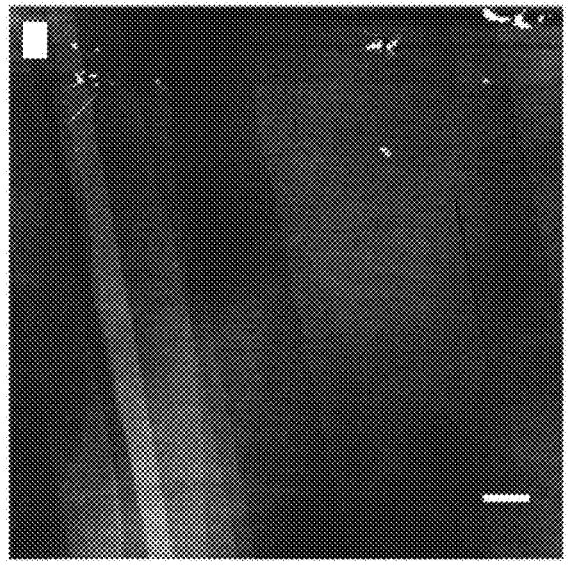
Figure 6D:
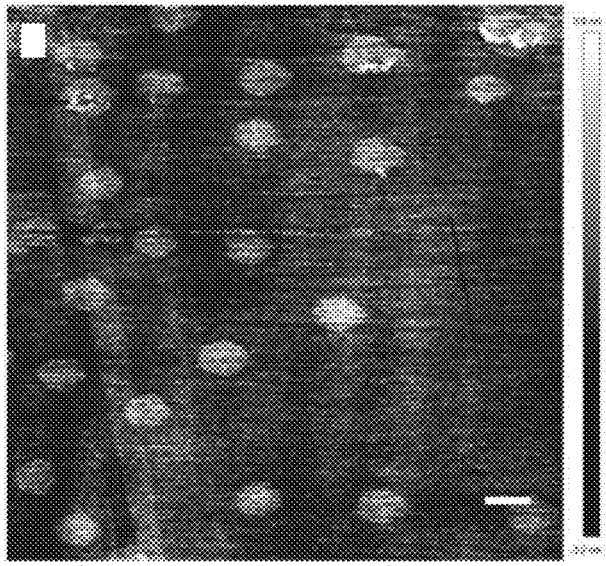

Due to the small hydrophilic fraction of Hex-ELP, the transition temperature ($T_t$) of Hex-ELP was found around 33° C., which is slightly higher when compared to the $T_t$ of ELP. At low temperature below $T_t$ of Hex-ELP, small objects and a few aggregates were observed with very low scattering intensity (30° C.). The scattering intensity sharply increased at transition temperature (around 33° C.) and triggered the self-assembly to form structures with hydrodynamic diameter ($D_h$) around 210 nm. The temperature-responsive behavior of Hex-ELP is fully reversible. When temperature was heated above 45° C., the nanoparticles showed little changes in scattering intensity and displayed diameter with a $D_h$ of approximately 400-500 nm (FIGS. 5A-5B).

Figure 7:
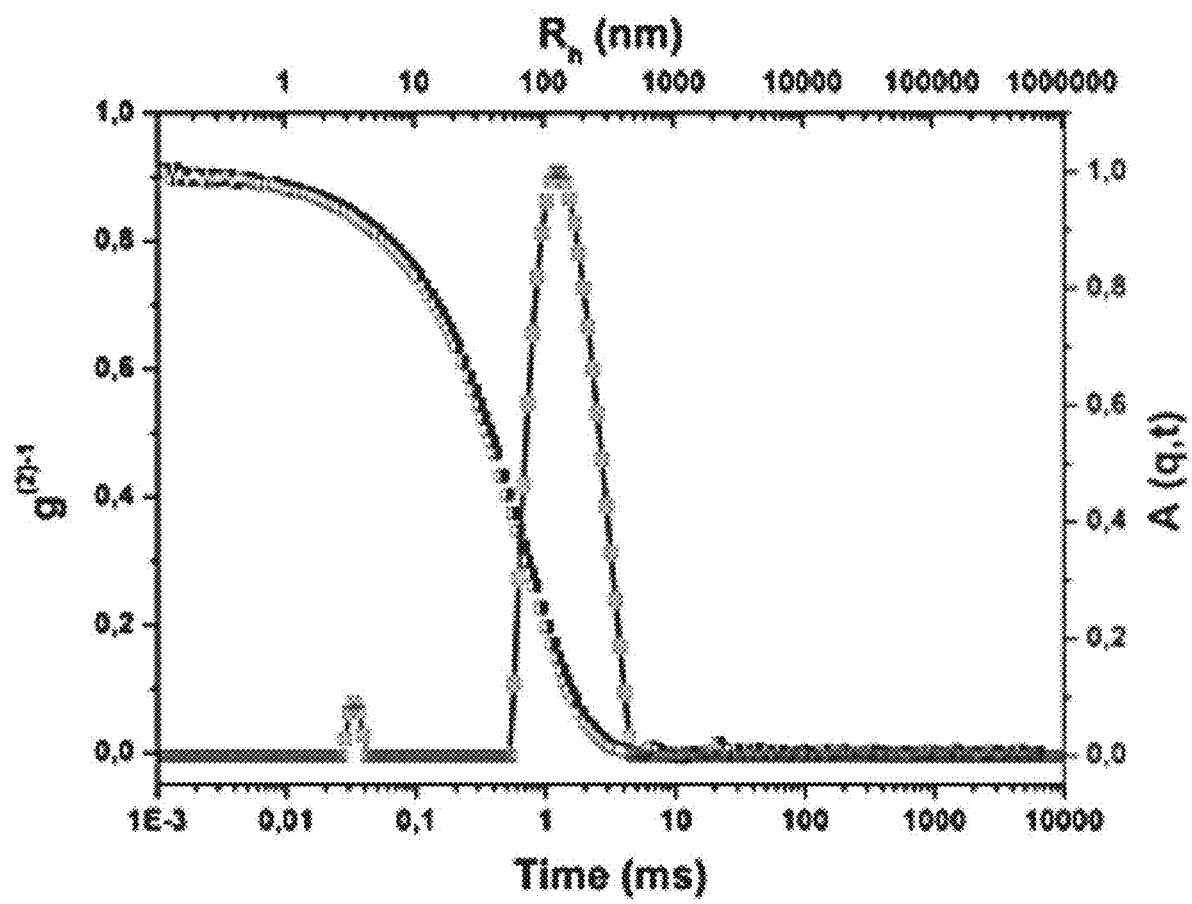
FIGS. 7, 8 and 9 represent DLS autocorrelation function $(g_2(t)-1)$ and relaxation-time distribution $(A(q,t))$ for Hex-ELP at 90°, FIG. 7 33° C., FIG. 8 37° C., and FIG. 9 45° C.
Figure 8:
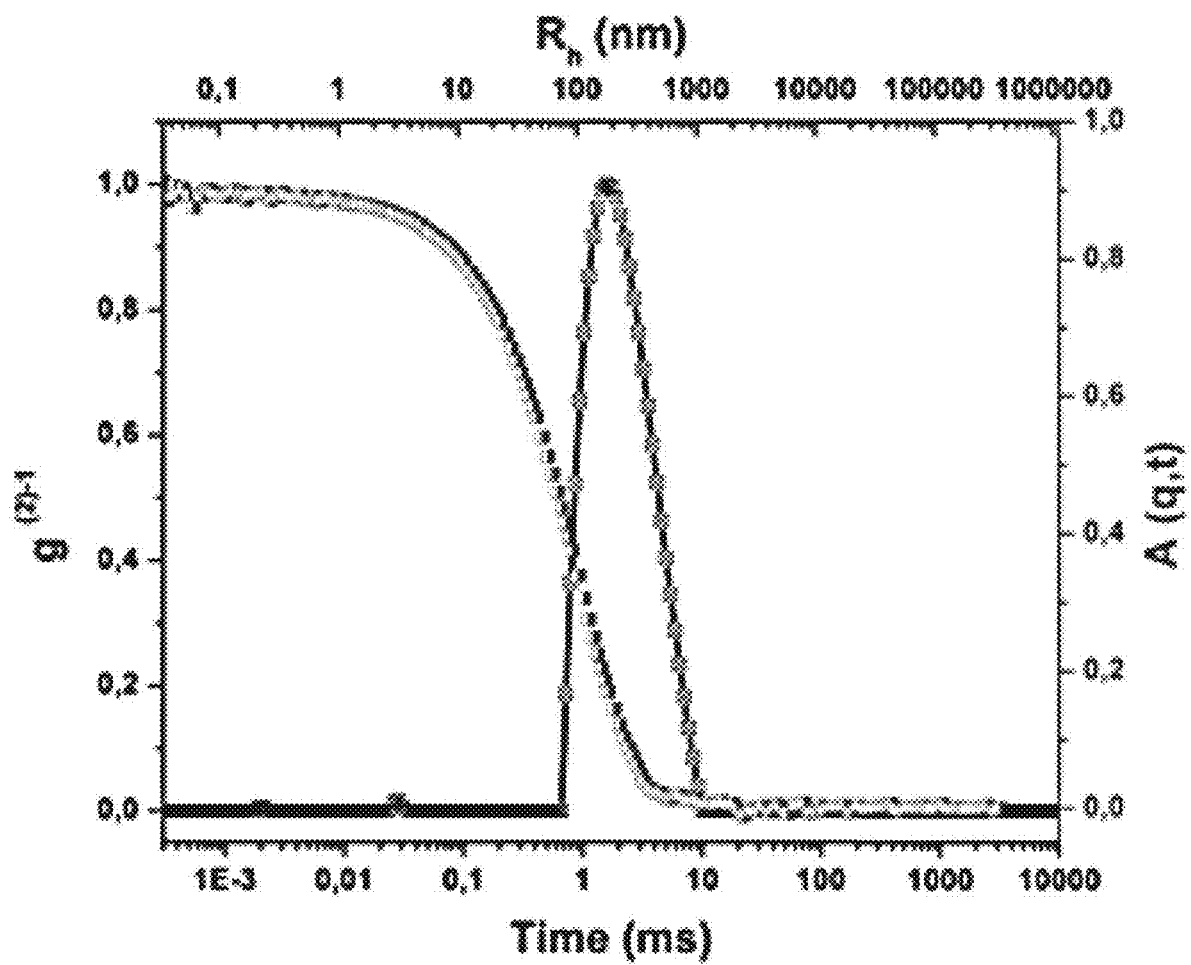
Figure 9:
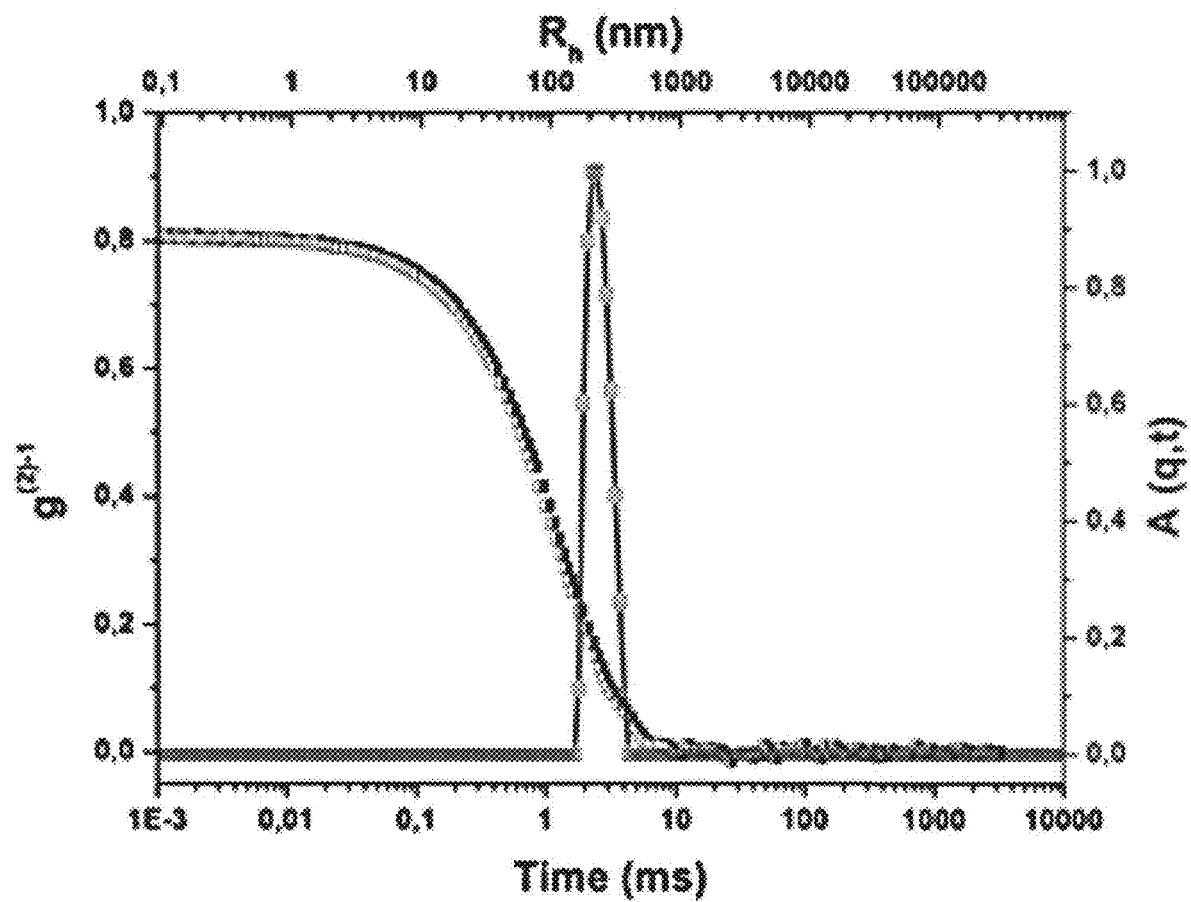

Hex-ELP assemblies were further analyzed by static light scattering at room temperature (25° C.), $T_t$ (33° C.), peak temperature (37° C.) and high temperature (45° C.). Consistent with DLS, Hex-ELP assemblies showed $D_h$ of approximately 250 nm and 500 at $T_t$ and 45° C. respectively (FIGS. 7-9). $R_g$ and $R_h$ at $T_t$ and high temperature were similar revealing relatively stable of the assemblies at high temperature. Similar to the SLS data, liquid AFM showed big diameters (500-900) for the aggregates of Hex-ELP (FIGS. 6A-6D).

TABLE 1

Value of $R_g$ and $R_h$ and $R_g/R_h$ ratio of Hex-ELP (125 µM in water).

| T (° C.) | $R_g$ (nm) | $R_h$ (nm) | $R_g/R_h$ |
|---|---|---|---|
| 25 | 36 | 24 | 1.5 |
| 33 | 100 | 130 | 0.77 |
| 37 | 140 | 259 | 0.54 |
| 45 | 128 | 252 | 0.51 |

Self-Assembly Study of HA-ELP

Figure 10:
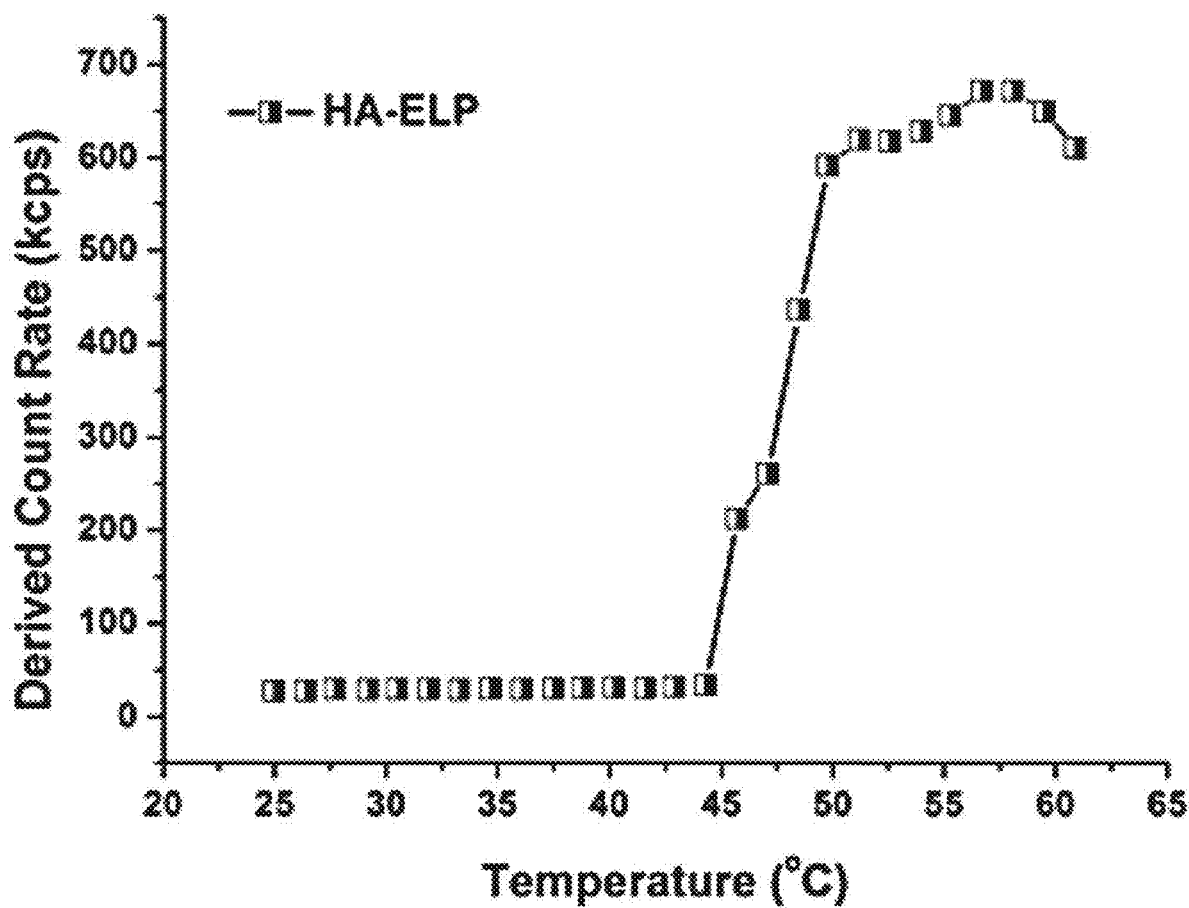
FIGS. 10 and 11 represent the dynamic light scattering analysis of the assembly of HA-ELP (150 µM) in water.
Figure 11:
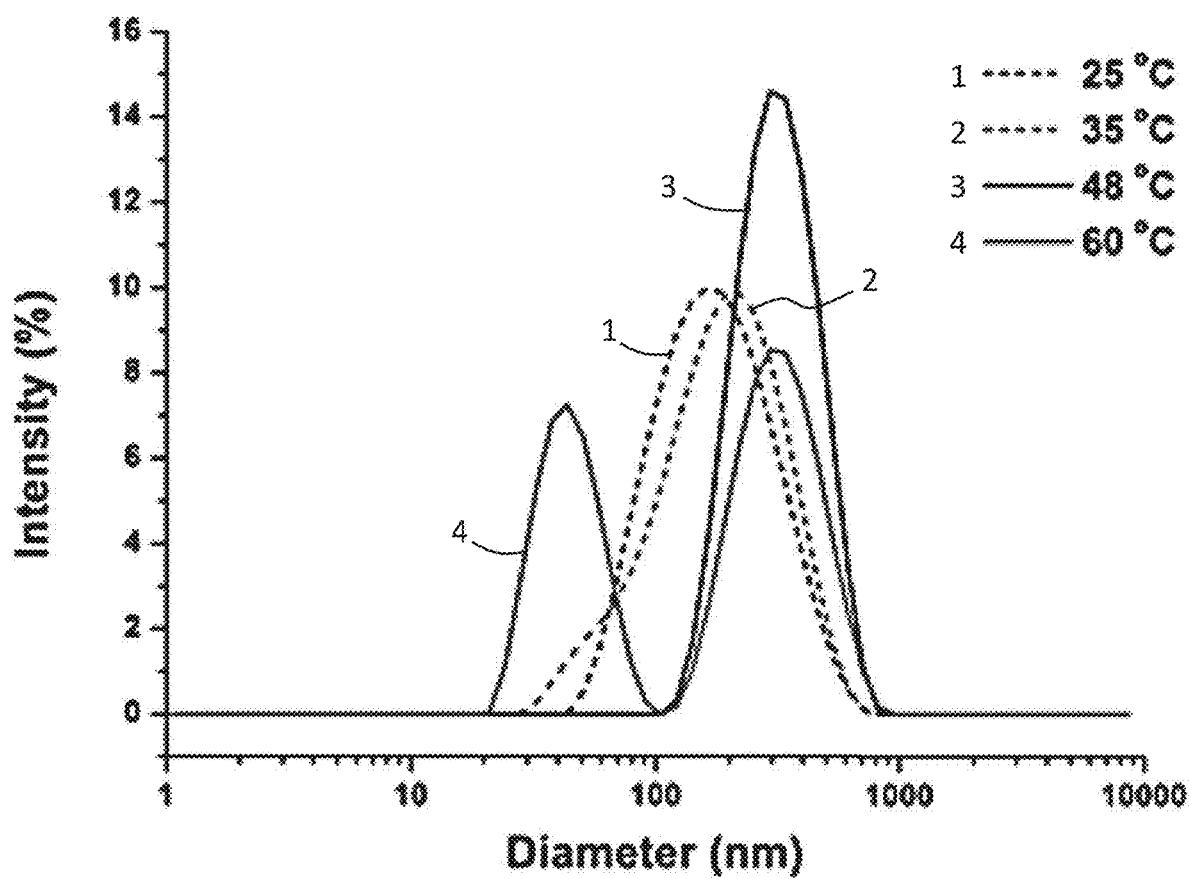

Similar to the UV-vis measurements, the $T_t$ of HA-ELP on DLS heating ramp was found around 45° C. At low temperature below $T_t$ of HA-ELP, small objects were observed with very low scattering intensity (35° C.). The scattering intensity sharply increased at transition temperature and triggered the self-assembly to form structures with $D_h$ around 300 nm at 48-50° C. (FIGS. 10-11). Once HA-ELP was heated above 55° C., the diameter of nanoparticles became unstable and separated into two size distributions, which is also confirmed by liquid AFM (FIG. 14A-F).

Figure 12:
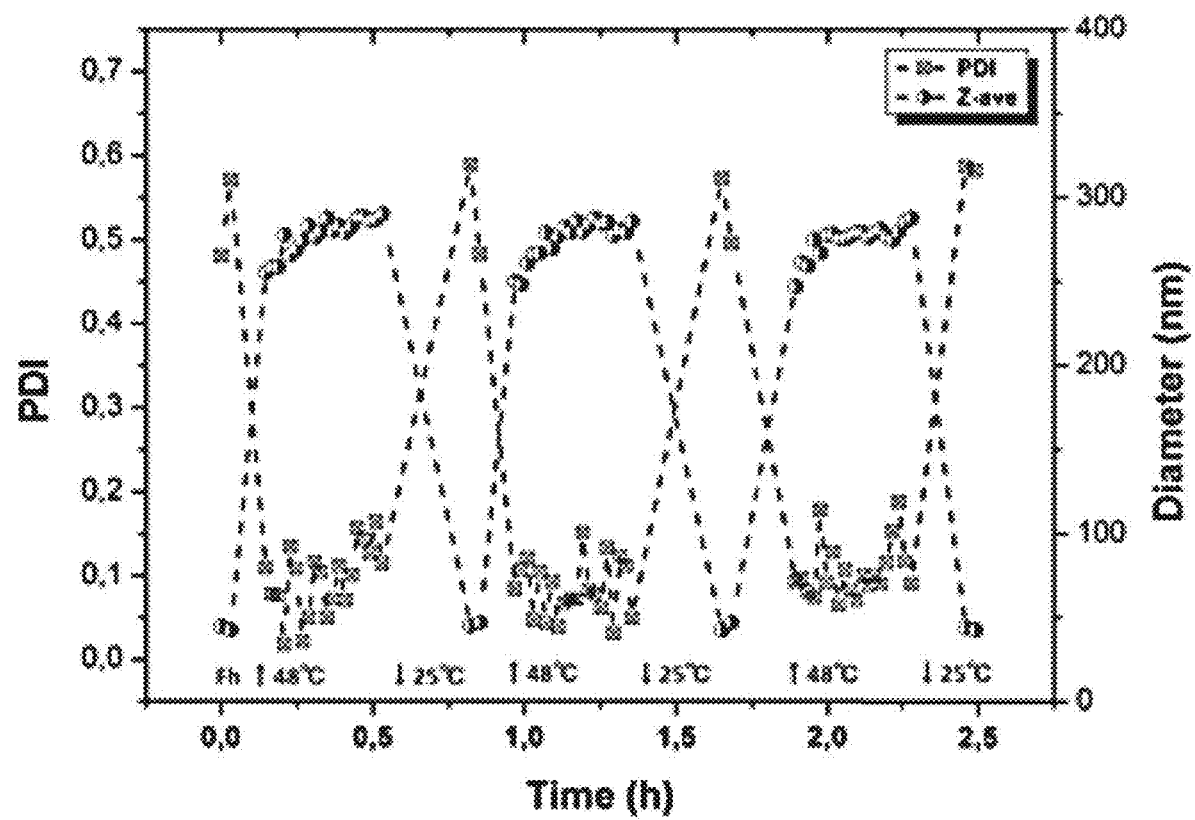
FIG. 12 represents Z-average size and polydispersity as a function of time upon repeated fast heating (48° C.) and cooling (25° C.) of HA-ELP (125 µM) in water on DLS.
Figure 13:
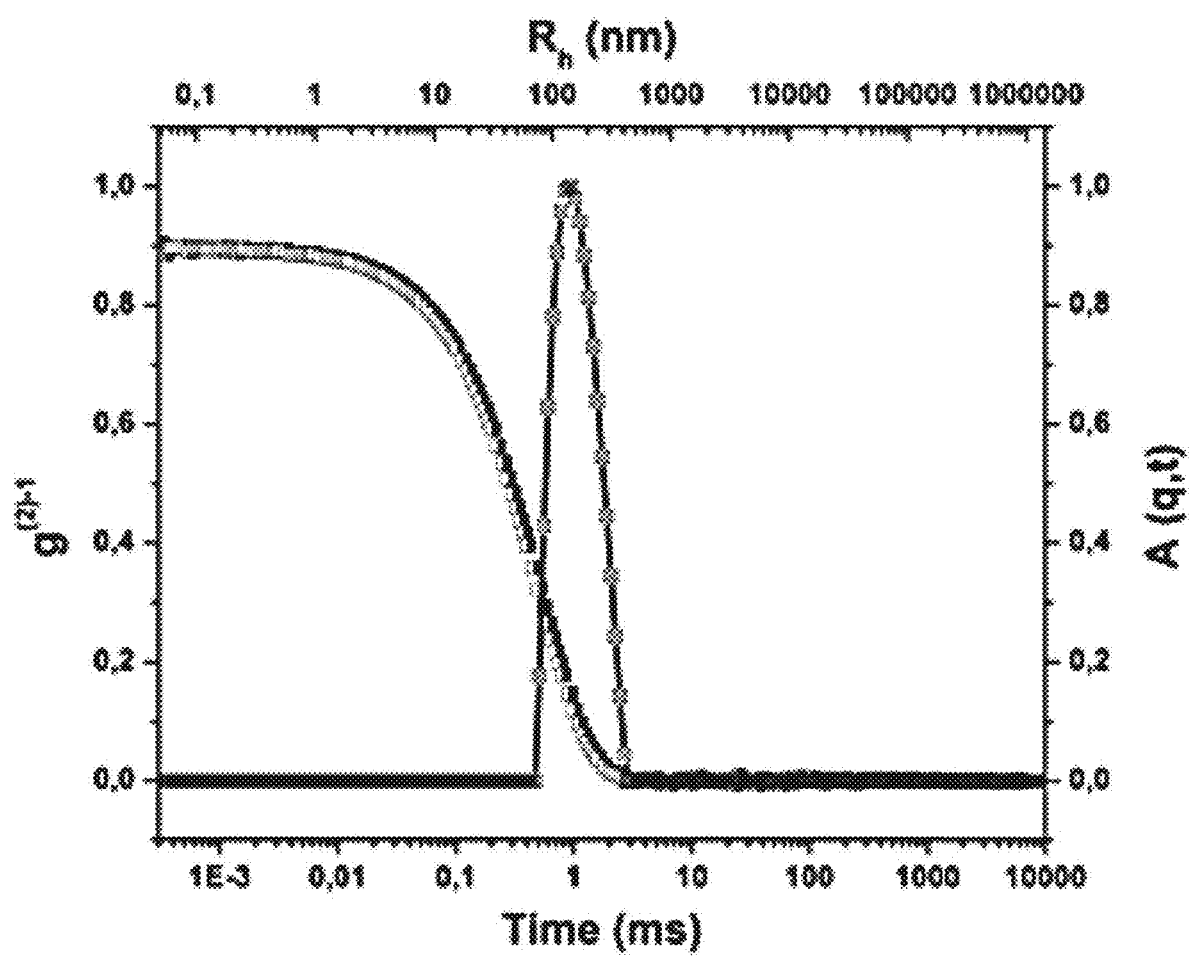
FIG. 13 represents DLS autocorrelation function $(g_2(t)-1)$ and relaxation-time distribution $(A(q,t))$ for HA-ELP (125 µM) in water at 50° C., 90°.

The stability of the HA-ELP assemblies at 48° C. was investigated by repeated heating and cooling on DLS. This temperature-responsive system is also fully reversible and HA-ELP showed relatively stable at 48° C. in 20 mins with average diameter around 280 nm on every single heating time (FIG. 12). Further analysis by static light scattering at 50° C. likewise illustrated $D_h$ at 304 nm (FIG. 13). $R_g/R_h$ ratio was calculated to be 0.79, indicating maybe micelle structure. Nanoparticles with an average diameter of approximately 220-280 nm were observed by liquid AFM at 50° C. (FIG. 14A-F) at the same concentration.

In conclusion, the bioconjugates mentioned above were able to self-assemble into particles in different sizes. The self-assembly characteristics were summarized in Table 2:

TABLE 2

| Copolymer | Conc. µM | $T_{t\,DLS}$ | DLS T/ ° C. | DLS $R_h$ nm | SLS T/ ° C. | SLS $R_g$ nm | SLS $R_h$ nm | ρ* | AFM T/ ° C. | AFM size/ nm |
|---|---|---|---|---|---|---|---|---|---|---|
| Dex-ELP | 125 | 39° C. | 45 | 300 | 45 | 132 | 183 | 0.72 | 35 | — |
|  |  |  |  |  |  |  |  |  | 65 | 190-340 |
| Hex-ELP | 125 | 33° C. | 33 | 210 | 33 | 100 | 130 | 0.77 | 30 | — |
|  |  |  | 45 | 520 | 45 | 128 | 252 | 0.51 | 55 | 500-900 |
| HA-ELP | 150 | 46° C. | 48 | 300 | 50 | 120 | 152 | 0.79 | 25 | — |
|  |  |  |  |  |  |  |  |  | 52 | 200-300 |

The self-assembly process was fully reversible by controlling the temperature which allows using these polysaccharide-ELP bioconjugates in biomaterial, drug delivery and receptor recognition.

The invention claimed is:

1. A block copolymer having at least one oligo- or polysaccharide block and at least one elastin-like polypeptide block, and having the following formula (II):

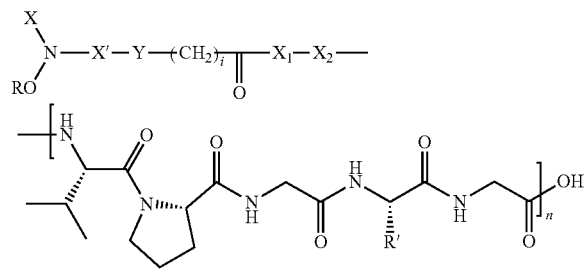

wherein:
- R is a $(C_1-C_6)$alkyl group,
- X is a oligo- or polysaccharide,
- X' is a $(C_1-C_6)$alkylene radical,
- Y is a radical selected from the group consisting of the following radicals:

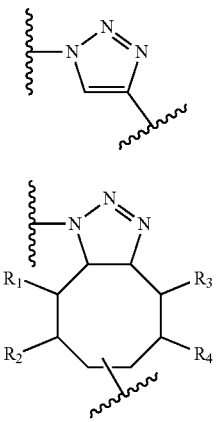

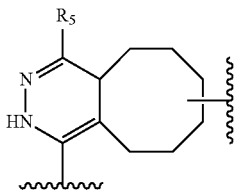

$R_1$ and $R_2$ being H or forming together with the carbon atoms carrying them a cyclohexyl radical;

$R_3$ and $R_4$ being H or forming together with the carbon atoms carrying them a cyclohexyl radical; and $R_5$ being H or an alkyl group;

i is an integer between 1 and 6, $X_1$ is a covalent bond or a radical of formula $X_2$ is a covalent bond or a radical of formula $-(AA)_j-$, j being an integer comprised between 1 and 6, and AA being independently a natural or synthetic amino acid, n is an integer between 1 and 200, and R' is the side chain of a natural or synthetic amino acid other than proline and derivatives thereof wherein the derivatives are selected from the group consisting of 4-hydroxy proline and α-methyl proline.

2. The block copolymer of claim 1, wherein R' is —CH$(CH_3)_2$ or —$(CH_2)_2SCH_3$.

3. The block copolymer of claim 1, having the following formula (III):

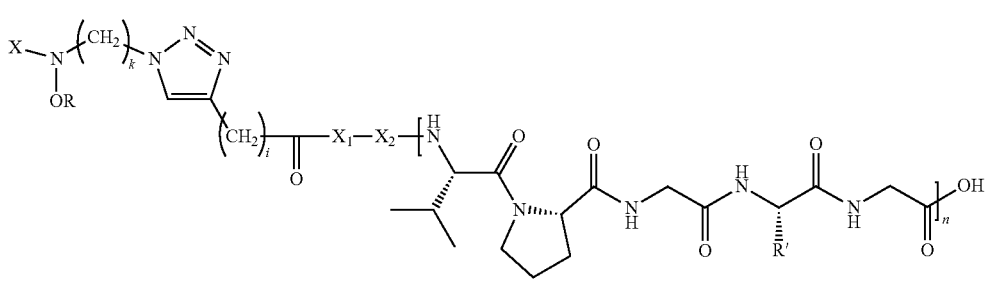

wherein:

k is an integer between 1 and 6, and i, n, X, $X_1$, $X_2$, R, and R' are as defined in claim 1.

4. The block copolymer of claim 1, having the following formula (III-1):

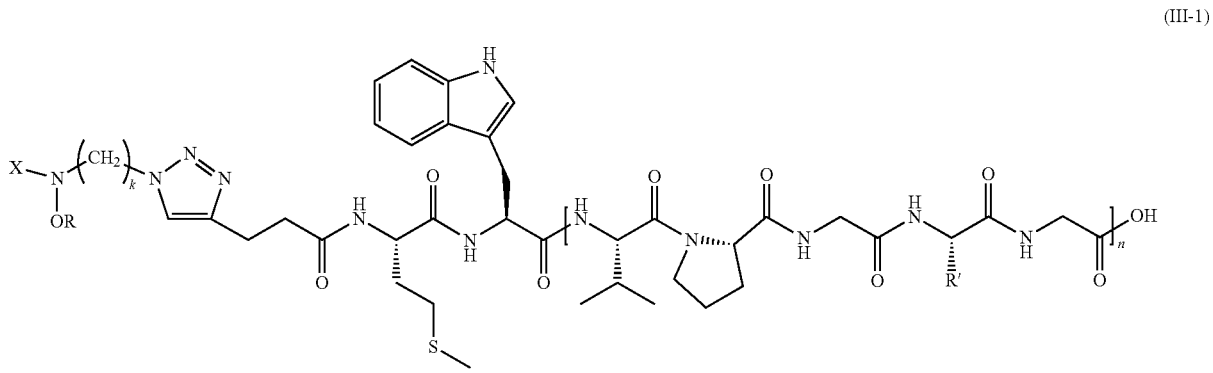

(III-1)

wherein:
k is an integer between 1 and 6, and
n, X, R, and R' are as defined in claim 1.

5. The block copolymer of claim 1, wherein X is a oligosaccharide or polysaccharide selected from the group consisting of: galactans, glycoaminoglycans, cellulose, chitosan and fucoidan.

6. The block copolymer of claim 5, wherein the oligosaccharide or polysaccharide is hyaluronan, laminarihexaose, dextran or a galactan.

7. The block copolymer of claim 1, having one of the following formulae:

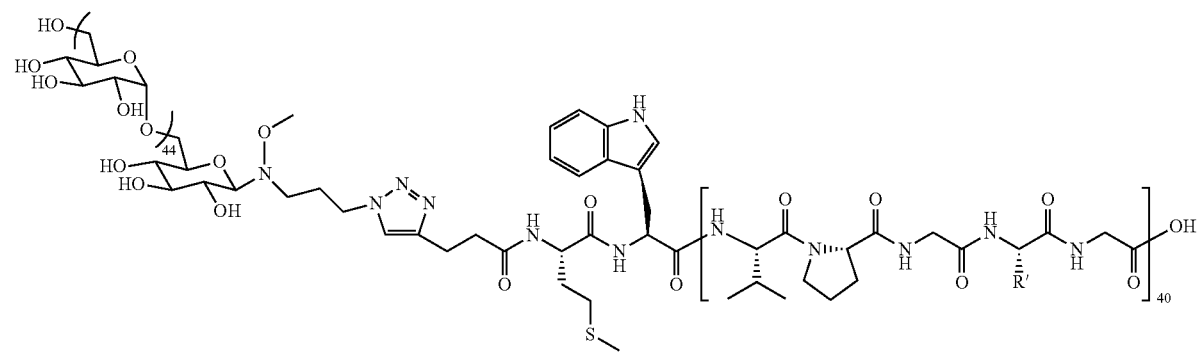

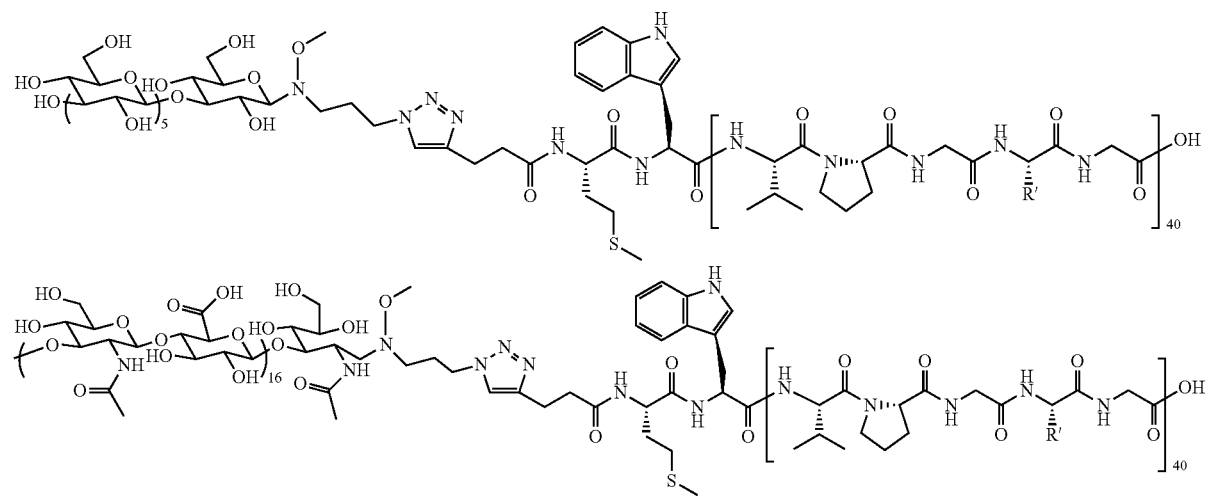

R' being as defined in claim 1.

8. A method for the preparation of a block copolymer of claim 1, comprising the reaction of a compound having the formula (IV):

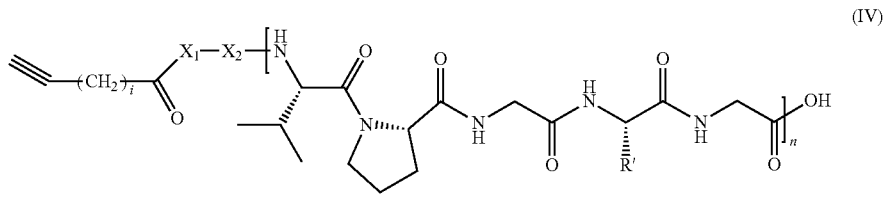
(IV)

wherein i, $X_1$, $X_2$, and R' are as defined in claim 1, with an azide compound having the formula (V):

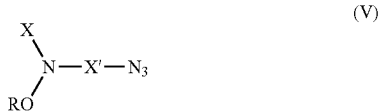
(V)

X, R, and X' being as defined in claim 1.

9. The method of claim 8, wherein the compound of formula (IV) is obtained by the reaction of a compound having the following formula (VI):

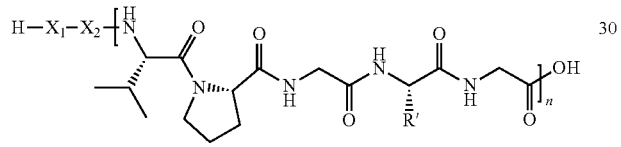

wherein
$X_1$ is a covalent bond or a radical of formula

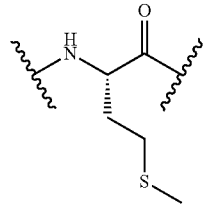

$X_2$ is a covalent bond or a radical of formula $-(AA)_j-$, j being an integer comprised between 1 and 6, and AA being independently a natural or synthetic amino acid, and R' is the side chain of a natural or synthetic amino acid other than proline and derivatives thereof, wherein the derivatives are selected from the group consisting of 4-hydroxy proline and α-methyl proline with a compound having the following formula (VII):

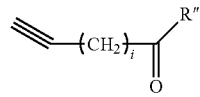

wherein:
i is an integer between 1 and 6, and
R" is a leaving group.

10. A method for the preparation of nanoparticles of a block copolymer as defined in claim 1, comprising a step of heating the block copolymer above its transition temperature.

11. The block copolymer of claim 3, wherein R' is —CH(CH$_3$)$_2$ or —(CH$_2$)$_2$SCH$_3$.

* * * * *